United States Patent [19]

Loscalzo et al.

[11] Patent Number: 5,025,001

[45] Date of Patent: Jun. 18, 1991

[54] S-NITROSO DERIVATIVES OF ACE INHIBITORS AND THE USE THEREOF

[75] Inventors: Joseph Loscalzo, Dedham; John Cooke, Needham Heights, both of Mass.

[73] Assignee: Brigham and Women's Hospital, Boston, Mass.

[21] Appl. No.: 328,397

[22] Filed: Mar. 24, 1989

Related U.S. Application Data

[63] Continuation-in-part of Ser. No. 206,763, Jun. 15, 1988.

[51] Int. Cl.$^5$ .................. A61K 31/505; A61K 31/54; A61K 31/425; A61K 31/40
[52] U.S. Cl. .................................... 514/91; 514/223.2; 514/259; 514/365; 514/412; 514/423; 544/12; 544/13; 544/287; 544/288; 544/289; 548/201; 548/413; 548/452; 548/533
[58] Field of Search .............. 548/201, 413, 452, 533; 514/365, 91, 223.2, 259, 412, 423; 544/12, 13, 287, 288, 289

[56] References Cited

U.S. PATENT DOCUMENTS

| | | | |
|---|---|---|---|
| 4,046,889 | 9/1977 | Ondetti et al. | 424/244 |
| 4,052,511 | 10/1977 | Cushman et al. | 424/274 |
| 4,053,651 | 10/1977 | Ondetti et al. | 548/336 X |
| 4,113,715 | 9/1978 | Ondetti et al. | 260/112.5 |
| 4,129,571 | 12/1978 | Ondetti et al. | 546/188 X |
| 4,154,840 | 5/1979 | Ondetti et al. | 546/188 X |
| 4,154,960 | 5/1979 | Ondetti et al. | 562/426 |
| 4,447,419 | 5/1984 | Quadro | 548/201 X |
| 4,461,896 | 7/1984 | Portlock | 546/165 |
| 4,568,675 | 2/1986 | Bush et al. | 514/250 |
| 4,585,758 | 4/1986 | Huang | 514/19 |
| 4,626,545 | 12/1986 | Taub | 514/423 |
| 4,681,866 | 7/1987 | Haugwitz et al. | 514/259 |
| 4,692,458 | 9/1987 | Ryan et al. | 514/362 |
| 4,692,459 | 9/1987 | Ryan et al. | 514/362 |
| 4,748,160 | 5/1988 | Bennion et al. | 562/439 |

FOREIGN PATENT DOCUMENTS

| | | |
|---|---|---|
| 0088341 | 9/1983 | European Pat. Off. |
| 0174162 | 3/1986 | European Pat. Off. |
| 0237239 | 9/1987 | European Pat. Off. |
| 0257485 | 3/1988 | European Pat. Off. |

OTHER PUBLICATIONS

Loscalzo, J. et al., *J. Clin. Invest.* 76:703–708 (1985).
Kadin, H. in *Analytical Profiles of Drug Substances* 11:79–137, Academic Press, N.Y. (1982).
Lidell, H. et al., *Analyst* 84:188–190 (1959).
Sieh, D. H. et al., *J. Pharm. Sci.* 73:1545–1547 (1984).
Ignarro, L. J. et al., *Biochem. Biophys. Acta* 631:221–231 (1980).
van Gilst, W. H. et al., *J. Cardiovasc. Pharmacol.* 9:254–255 (1987).
van Gilst, W. H. et al., *Circ. Suppl. II* 78:II. 221 (Abstr. 0882) (1988).
Horowitz, J. D. et al., *Circulation* 68:1247–1253 (1983).
Cushman, D. W. et al., *Biochemistry* 16:5484–5491 (1977).
Drummer, O. H. et al. *Pharmacology* 545–550 (1987).
Ondetti, M. A., *Circulation* 77 (Suppl. I) 74–78 (1988).
The International Search Report for the corresponding International application.

*Primary Examiner*—Joseph Paul Brust
*Attorney, Agent, or Firm*—Sterne, Kessler, Goldstein & Fox

[57] ABSTRACT

The invention relates to novel S-nitroso derivatives of ACE inhibitors and to pharmaceutical compositions comprising the S-nitrosothiol derivatives of the invention together with a pharmaceutically acceptable carrier.

The invention also relates to methods for treating various pathophysiological conditions including acute myocardial infarction, left ventricular dysfunction without overt heart failure, hypertension, pulmonary hypertension, congestive heart failure, angina pectoris, vascular thrombosis, Raynauds syndrome, scleroderma, toxemia of pregnancy, acute renal failure, diabetic nephropathy, and renal artery stenosis, and to methods of inhibiting ACE and effecting vasodilation comprising administering the S-nitrosothiol derivatives of the ACE inhibitors of the invention to an animal.

22 Claims, 6 Drawing Sheets

RELAXATION TO SnoCap: BOVINE CORONARY ARTERY

S-NITROSO DERIVATIVES OF ACE INHIBITORS AND THE USE THEREOF

CROSS REFERENCE TO RELATED APPLICATION

This application is a continuation-in-part of U.S. Application Serial No. 07/206,763 filed June 15, 1988.

FIELD OF THE INVENTION

This invention relates to new pharmaceutical preparations and the use thereof for the treatment of various pathophysiological diseases including acute myocardial infarction, left ventricular dysfunction without overt heart failure, congestive heart failure, angina pectoris, vascular thrombosis, hypertension, Raynauds syndrome, scleroderma, toxemia of pregnancy, acute renal failure, diabetic nephropathy, renal artery stenosis, and pulmonary hypertension. The invention also relates to methods for inhibiting ACE and effecting vasodilation by administering the pharmaceutical preparations of the invention to an animal.

BACKGROUND OF THE INVENTION

A variety of vasodilators currently exist for the treatment of hypertensive states, angina pectoris, and congestive heart failure. These agents may be classified according to their primary mechanism of action. Two important groups of these agents are the angiotensin converting enzyme inhibitors (useful in hypertension and congestive heart failure, but not angina) and nitrates (useful in angina and congestive heart failure, but less effective in hypertension). Neither of these groups are believed to be clinically important as antiplatelet agents.

Angiotensin converting enzyme (ACE) is capable of converting angiotensin I to angiotensin II by removal of the carboxy terminal His-Leu. Angiotensin II is formed by the action of the enzyme renin and endopeptidase found in the kidney, other tissues, and plasma. Blood pressure is affected by various peptides found in the blood including angiotensin II. Angiotensin II is reported to be a powerful pressor agent found at elevated concentrations in the blood of patients with renal hypertension.

The level of ACE activity is ordinarily in excess, in both normal and hypertensive patients, of the amount needed to maintain observed levels of angiotensin II. However, it has been found that significant blood pressure lowering is achieved in hypertensive patients by treatment with ACE inhibitors (Gavras, I , et al.. *New Engl. J. Med.* 291:817 (1974)). The role of ACE in the pathogenesis of hypertension has prompted a search for inhibitors of the enzyme that could act as antihypertensive drugs. A highly effective inhibitor, with high biological activity when orally administered, is D-3-mercapto-2-methylpropanoyl-L-proline, also known as captopril. Ondetti et al., U.S. Patent No. 4,046,889 (1977); Cushman, D. W., et al.. *Biochemistry* 16.5484 (1977); and Ondetti, M., et al.. *Science* 196.441 (1977).

Captopril is believed to act by binding to the ACE active site. In early studies, the active site was postulated to be cationic and binding for the carboxyl end group of the substrate in a pocket or cleft. This pocket was believed to be capable of binding the side chain of the C-terminal amino acid and providing especially tight binding for the heterocyclic ring of a terminal proline residue. A similar pocket for the penultimate amino acid residue was postulated. The published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as the methyl group, and an S-acetyl derivative, reportedly reduce the potency of the inhibitor. See Ryan et al.. U.S. Pat. No. 4,692,458 (1987); and Cushman, D. W.. et al., *Biochemistry, supra.*

In an effort to increase the stability and potency of captopril, a number of analogs have been prepared. See, for example, Ondetti et al.. U.S. Pat. Nos. 4,046,889 (1977), 4,052,511, 4,053,651, 4,113,751, 4,154,840, 4,129,571 (1978), and 4,154,960 (1979); Taub, U.S. Pat. No. 4,626,545 (1986); and Ryan et al.. U.S. Pat. Nos. 4,692,458 (1987) and 4,692,459 (1987).

Quadro, U.S. Pat. No. 4,447,419 (1984), disclose that 3-[N-(2-mercapto-propionyl-amino-acetyl)]-tetrahydrothiazolyl-4-carboxylic acid having the Formula (I):

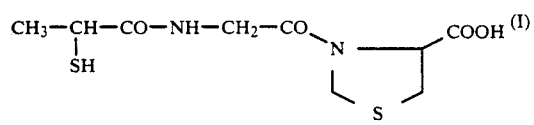

is an ACE inhibitor.

Haugwitz et al.. U.S. Pat. No. 4,681,886 (1987), disclose that the 4-phenoxy and 4-phenylthio substituted proline derivatives having Formula (II):

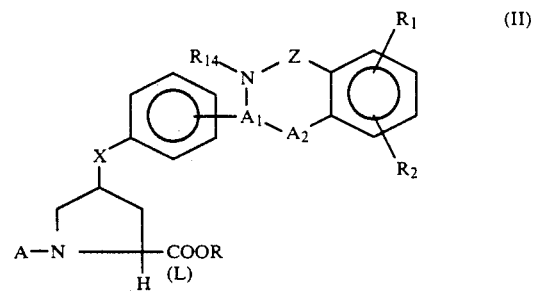

are ACE inhibitors.

Bush et al., U.S. Pat. No. 4,568,675 (1986), disclose that 3,6-dihydroxyphenazine-1-carboxylic acid having the Formula (III):

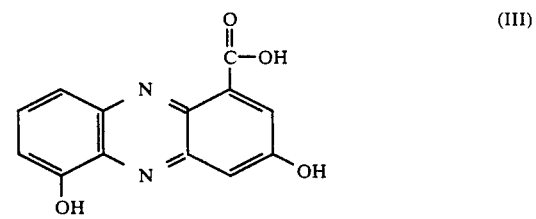

is an ACE inhibitor.

Bennion et al.. U.S. Pat. No. 4,748,160 (1988), disclose that compounds of the Formula (IV):

$$ZCHRCON(-N=CR_4R_5)CHR_6(CH_2)_nCOY \qquad (IV)$$

are ACE inhibitors.

Portlock, U.S. Pat. No. 4,461,896 (1984), disclose that 1-acylthio) and (mercapto)-1-oxoalkyl]-,1,2,3,4-tetrahydroquinoline-2-carboxylic acids having Formula (V):

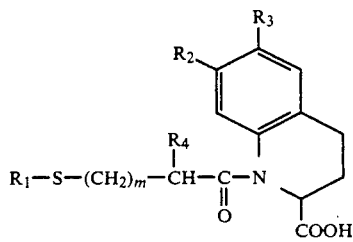
(V)

are ACE inhibitors.

Hoefle et al.. European Patent application Publication No. 0 008 341 (1983), disclose that the substituted acyl derivative of octahydro-1H-indole-2-carboxylic acid having the Formula (VI):

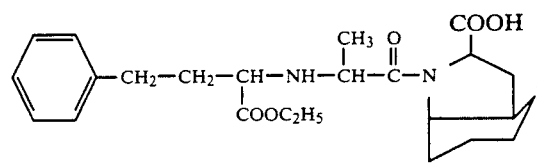

are ACE inhibitors.

Huange et al., U.S. Pat. No. 4,585,758 (1986), disclose that compounds having the Formula (VII):

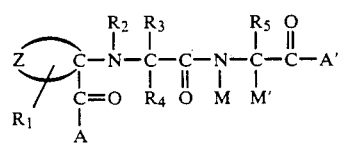
(VII)

are ACE inhibitors.

European Patent application Publication No. 0 237 239, published in 1987, discloses that compounds of the Formula (VIII):

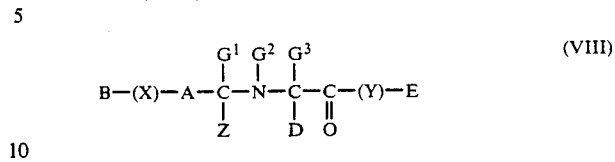
(VIII)

are ACE inhibitors and beta blockers.

European Patent application Publication No. 0 174 162, published in 1986, discloses that compounds of the Formula (IX):

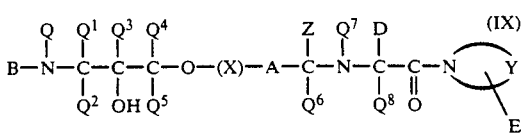
(IX)

are ACE inhibitors.

European Patent application Publication No. 0 257 485, published in 1988, discloses that compounds of the Formulae (X) and (XI):

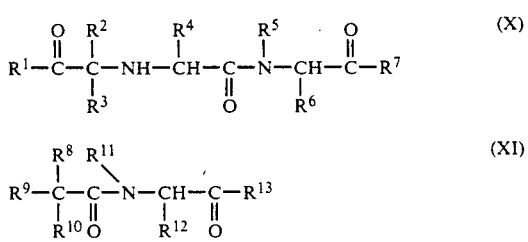

are ACE inhibitors.

Ondetti, M. A., *Circulation* 77(suppl. I) 74–78 (1988), disclose a structure-activity study of ACE inhibitors having the following Formulae:

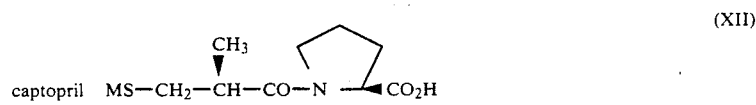
(XII)

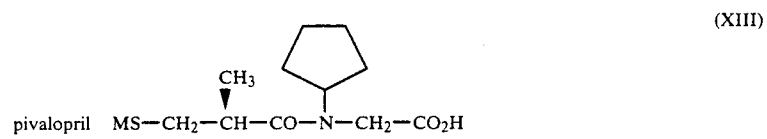
(XIII)

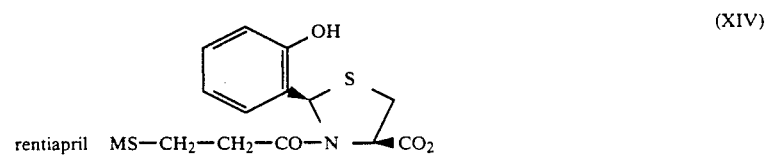
(XIV)

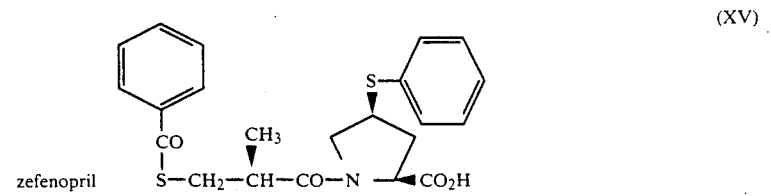
(XV)

enalapril 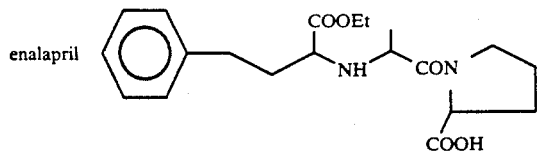 (XVI)
ramipril 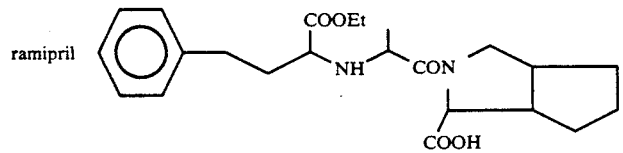 (XVII)
(XVIII)
quinapril 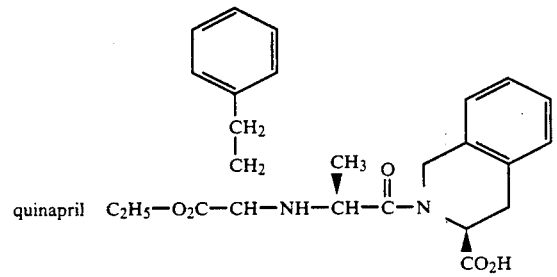
perindopril 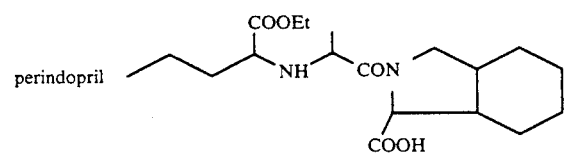 (XIX)
cilazapril 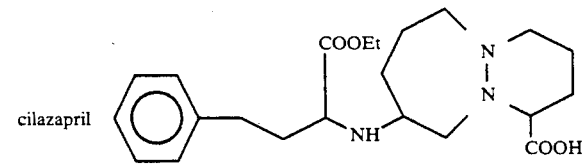 (XX)
delapril 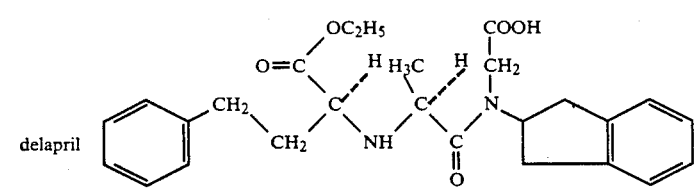 (XXI)
lisinopril 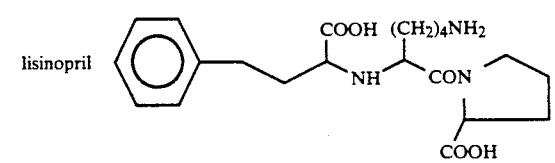 (XXII)
(XXIII)
fosinopril 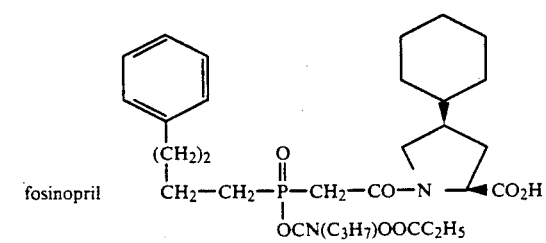

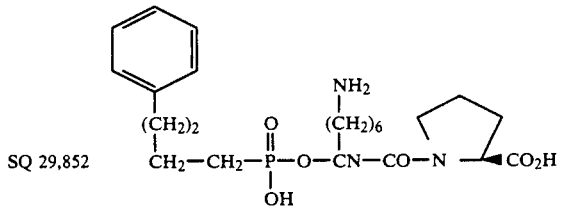

SQ 29,852

Drummer, O. H. et al., *Pharmacology* 545–550 (1987), disclose a structure-activity relationship study of ACE inhibitors including:

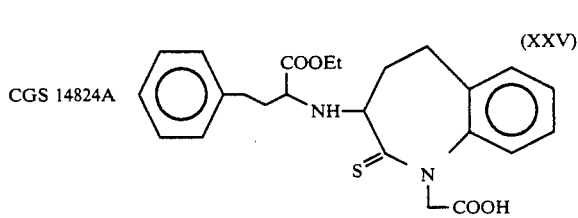

CGS 14824A

In contrast to ACE inhibitors, organic nitrate vasodilators (of which nitroglycerin is the prototypic compound) are direct smooth muscle relaxants that likely act by activating guanylate cyclase. These compounds are believed to be metabolized intracellularly to active intermediate forms, S-nitrosothiols, that in turn transfer the active nitrous oxide moiety to the heme activator site of guanylate cyclase and, thereby, lead to increased production of cyclic GMP and attendant smooth muscle relaxation. As with the ACE inhibitors, organic nitrates do not act on any specific regional arterial bed with selectivity, all beds being dilated relatively equivalently. Ignarro, L. J., et al.. *Biochem. Biophys. Acta* 631:221-231 (1980) showed that the S-nitrosothiols of cysteine, penicillamine, glutathione, and dithiothreitol are capable of activating soluble guanylate cyclase. The authors suggest that S-nitrosothiols could act as intermediates in the activation of guanylate cyclase by glycerol trinitrate, $NaNO_2$, and possibly nitroprusside.

Horowitz, J. D., et al., *Circulation* 68:1247-1253 (1983), disclose that the vasodilator action of nitroglycerin may be closely linked to the availability of critical SH groups in vascular smooth muscle. The authors postulate that the activity of nitroglycerin is modulated through the formation of S-nitrosothiol compounds, which are formed by the interaction of nitroglycerin with tissue sulfhydryl groups. In fact, tolerance commonly develops to organic nitrates. This is believed to be a result of depletion of critical tissue sulfhydryl compounds, the exact chemical nature of which remains to be identified. Among the S-nitrosothiols disclosed to be potent activators of guanylate cyclase in arterial smooth muscle were the S-nitroso derivatives of cysteine, dithiothreitol, penicillamine, and reduced glutathione. Ascorbate was found to be totally ineffective.

Loscalzo, J., et al.. *J. Clin. Invest.* 76:703-708 (1985), disclose the preparation of S-nitroso-N-acetyl cysteine. This compound is reported to be an extremely potent inhibitor of platelet aggregation.

Reports concerning development of pharmaceutical agents that lower blood pressure, improve congestive heart failure, or hasten resolution of anginal episodes notwithstanding, a need continues to exist for medicants that are useful in the treatment of these disorders particularly if they are shown to exhibit the following properties: 1) the agent should have a prompt onset of action and a lengthy duration of action; 2) the use of the agent should not be associated with the development of the tolerant state; 3) the agent should ideally be relatively coronary selective; 4) the agent should be equally useful in the treatment of all three of these disorders since they commonly occur in the same patient--i.e., the hypertensive patient with coronary artery disease manifesting as angina pectoris and chronic congestive heart failure; and 5) since platelets are important in the pathophysiology of ischemic heart disease states like angina pectoris, antiplatelet effects would be a very useful additional property.

SUMMARY OF THE INVENTION

The invention relates to S-nitrosothiol derivatives of ACE inhibitors.

In particular, the invention relates to S-nitrosothiol derivatives of ACE inhibitors having the Formula (XXVI):

wherein

R is hydroxy, $NH_2$, $NHR^4$, $NR^4R^5$ or $C_1$-$C_7$ alkoxy, wherein $R^4$ and $R^5$ are $C_1$-$C_4$ alkyl, aryl, or $C_1$-$C_4$ alkyl substituted by aryl;

$R^1$ is hydrogen, $C_1$-$C_7$ alkyl or $C_1$-$C_7$ alkyl substituted by phenyl, amino, guanidino, $NHR^6$ or $NR^6R^7$, wherein $R^6$ and $R^7$ are methyl, or $C_1$-$C_4$ acyl;

$R^3$ is hydrogen, $C_1$-$C_7$ alkyl or $C_1$-$C_7$ alkyl substituted by phenyl;

n is 0 to 2;

A is hydrogen,
  lower $C_1$-$C_7$ alkyl,
  lower $C_2$-$C_7$ alkylene,
  kiwer $C_2$-$C_7$ alkylene substituted by hydroxy, $C_1$-$C_4$ alkyl, aryl, or
  a $C_4$-$C_7$ ring which may be fused to a benzene ring;

B is hydrogen,
  lower $C_1$-$C_7$ alkyl,
  phenyl,
  lower $C_1$-$C_7$ alkyl substituted by phenyl, hydroxy, guanidino, amino, imidazolyl, indolyl, mercapto, mercapto substituted by lower $C_1$-$C_4$ alkyl, carbamoyl, or carboxy, or
  lower $C_2$-$C_7$ alkylene.

The invention also related to S-nitrosothiol derivatives of ACE inhibitors having the following Formula (XXVII):

$$\underset{\text{(XXVII)}}{\overset{R^3}{\underset{|}{\text{ON}}}-S-(CH)_n-\overset{R^1}{\underset{|}{\text{CH}}}-\overset{O}{\underset{\|}{\text{C}}}-\overset{CH_2-(CH)_m}{\underset{|}{\text{N}}}-\overset{O}{\underset{\|}{\text{C}}}-R}$$

wherein R, $R^1$, $R^3$ and n are as defined above;

$R^2$ is hydrogen, hydroxy, $C_1$-$C_4$ alkoxy, aryloxy or $C_1$-$C_4$ alkyl; and m is 1 to 3.

The invention also relates to the S-nitrosothiol having the Formula (XXVIII)

$$\underset{\text{(XXVIII)}}{CH_3-\underset{\underset{SNO}{|}}{CH}-CO-NH-CH_2-CO-N\begin{array}{c}CHCOOH\\ |\\ S\end{array}}$$

The invention also relates to compounds of the Formula (XXIX):

(XXIX)

[structure shown]

wherein

X is oxygen or sulfur;

—$A_1$—$A_2$— is —CH—NH or —C=N—;

$$A \text{ is } ON-S-CH_2-\overset{R_3}{\underset{|}{CH}}-\overset{O}{\underset{\|}{C}}-;$$

A is ON-S-$CH_2$-CH-C-;

R is selected from hydrogen, lower ($C_1$-$C_4$) alkyl, benzyl, benzhydryl, and salt forming ion;

$R_1$ and $R_2$ are independently selected from hydrogen, halogen, lower alkyl, lower alkoxy, halo substituted lower alkyl, nitro, and -$SO_2NH_2$;

Z is $$-\overset{O}{\underset{\|}{C}}- \text{ or } -\overset{O}{\underset{\underset{O}{\|}}{S}}-\,;$$

$R_3$ is hydrogen, lower alkyl, halo substituted lower alkyl, phenyl, benzyl, phenethyl, or cycloalkyl;

$R_{14}$ is hydrogen, lower alkyl, cycloalkyl-$(CH_2)_n$-, wherein n is 1, 2, 3, or 4;

[phenyl structure with $R_6$ and $(CH_2)_n$—]

halo substituted lower alkyl, hydroxy substituted lower alkyl, —$(CH_2)_q$-N(lower alkyl)$_2$, or —$(CH_2)_q$—$NH_2$, wherein q is 1, 2, 3, or 4; and $R_6$ is hydrogen, lower alkyl, lower alkoxy, halogen, or hydroxy.

The invention also relates to compounds of the Formula (XXXI):

(XXXI)

[phenazine-like structure with ON—S—$CH_2(CH_2)_n$C—O— substituent]

wherein n is 1-5.

The invention also relates to compounds of the Formula (XXXII):

$$ZCHRCON(-N=CR_4R_5)CHR_6(CH_2)_nCOY \qquad \text{(XXXII)}$$

in which

Z is ON—$SCH_2$—,

Ph is phenyl,

R is hydrogen or $C_1$-$C_{10}$ alkyl, $R_4$ and $R_5$, which may be the same or different, are each hydrogen, phenyl, naphthyl; a 5 or 6 membered alicyclic or heterocyclic ring each of which is optionally fused to a benzene ring; cycloalkyl containing 3 to 7 carbon atoms; or $C_1$-$C_{10}$ alkyl optionally substituted by phenyl, naphthyl or a 5 or 6 membered heterocyclic ring which latter is optionally fused to a benzene ring, the phenyl, naphthyl or 5 or 6 membered alicyclic or heterocyclic ring (which latter two are optionally fused to a benzene ring) are all optionally substituted by one or more $C_1$-$C_{10}$ alkyl, $C_1$-$C_{10}$ alkoxy, halogen, $C_7$-$C_{12}$ phenylalkyl, $C_7$-$C_{12}$ phenylalkoxy, phenyl, hydroxy, carbonyl, $C_1$-$C_{10}$ fluoroalkyl, cyano, nitro, phenylsulphonamido, $C_2$-$C_{20}$ dialkyl-amino-alkoxy, $C_1$-$C_{10}$ alkylthio, or $C_2$-$C_{20}$ dialkyl-amino, or $R_4$ and $R_5$ together form a —$(CH_2)_4$—, —$(CH_2)_5$—,

[structures shown with $(CH_2)_q$] or [adamantane] chain $R_6$ is hydrogen or $C_1$-$C_{10}$ alkyl, q is 2 or 3, n is 0 or 1, Y is hydroxy or —$NHSO_2R_9$, and $R_9$ is $C_1$-$C_{10}$ alkyl, and pharmaceutically acceptable salts, esters, and amides thereof.

The invention also relates to compounds of the Formula (XXXIII):

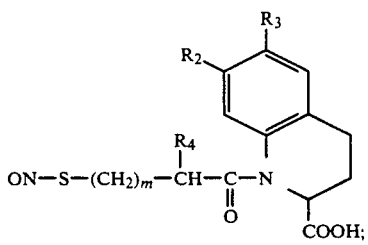

(XXXIII)

$R_2$ is hydrogen, methoxy, or methyl; $R_3$ is hydrogen, methoxy, methyl, chloro, or hydroxy; $R_4$ is hydrogen, methyl or acetylthiomethyl; m is 0 or 1 and the sodium and dicyclohexylamine salts thereof.

The invention also relates to compounds of the Formula (XXXIV):

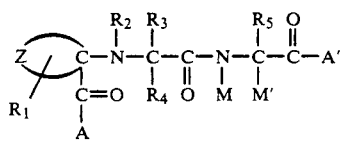

(XXXIV)

and their pharmaceutically acceptable salts, wherein

A and A' are independently hydroxy, lower alkoxy, lower alkenoxy, mono- or di-loweralkylamino-loweralkoxy, acylamino-lower-alkoxy, acyloxy-lower-alkoxy, aryloxy, aryl-loweralkyloxy, amino, loweralkylamino, di-loweralkylamino, aryl-loweralkylamino, hydroxyamino, or substituted aryloxy, or substituted aryl-loweralkoxy wherein the substituent is methyl, halo, or methoxy;

$R_1$ is hydrogen, lower alkyl, aryl, aralkyl, fused cycloalkylaryl, or fused aryl-cycloalkyl;

$R_2$, $R_3$, $R_4$ and $R_5$ are independently hydrogen, lower alkyl, lower alkenyl, lower alkynyl, aryl, fused cycloalakyl-aryl, fused arylcycloalkyl, aralkyl, cycloalkyl, or heterocyclic, or wherein $R_2$ and $R_3$ taken together with the nitrogen and carbon atoms to which they are respectively attached form an N-heterocyclic ring containing from 3 to 5 carbon atoms or 2 to 4 carbon atoms and a sulfur atom;

M is hydrogen, alkyl, alkenyl, alkynyl, cycloalkyl, acyl, cycloalkyl-alkyl, polycycloalkyl, polycycloalkyl-alkyl, aryl-aralkyl, heteroaryl, heteroaryl-alkyl, heterocycloalkyl, heterocycloalkylalkyl, fused polycyclic aryl, fused cycloalkyl-aryl, fused arylcycloalkyl, fused aryl-cycloalkyl-alkyl, fused heteroaryl-cycloalkyl, fused heteroaryl-cycloalkyl-alkyl, alkoxyalkyl, alkylthioalkyl, alkyl-amino-alkyl, or dialkylaminoalkyl, M' is hydrogen, loweralkyl, cycloalkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkyl thio lower alkyl, or M and M' may be connected together to form a saturated or unsaturated bridge of from 2 to 5 carbon atoms; from 2 to 4 carbon atoms and one oxygen or sulfur atom; fused aralkylene; fused cycloalkyl-alkylene; or a bridge as above, or fused aralkylene, substituted with hydroxy, lower alkoxy, or lower alkyl; and Z contains 2, 3, 4 or 5 carbon atoms, and optionally an O, N or S atom, and is saturated or contains at most one double bond between adjacent carbon atoms;

wherein the alkyl, alkenyl, and alkynyl groups may carry substituents selected from the group consisting of hydroxy, alkoxy, amino, mono- or dialkylamino, thio, and alkylmercapto; and cycloalkyl groups may carry substituents selected from the group consisting of alkyl, hydroxy, alkylamino, nitro and trifluoromethyl; and the aryl, fused ring, and heterocyclic groups may carry substituents selected from the group consisting of carboxylic acid, lower alkoxycarbonyl, alkyl, hydroxy, alkoxy, hydroxyalkyl, halo, haloalkyl, alkyl-thio, mercaptoalkyl, amino, alkylamino, aminoalkyl, nitro, and methylenedioxy, and trifluoromethyl, and wherein at least one of the alkyl, alkenyl and alkynyl groups is substituted by —S—NO.

The invention also relates to compounds of the Formula (XXXV):

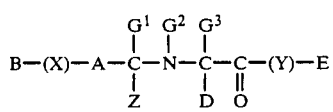

(XXXV)

A is a group of formula $-Q_k-(NQ^1)_m-(CH_2)_n-$, where k and m are independently selected from 0 and 1, provided that m can only be 0 when k is 0, n is from 1 to 6, $Q^1$ is hydrogen or $C_{1-4}$ alkyl, Q is selected from —CO—, —CH$_2$—, —CH$_2$CO— and —OCH$_2$CO—, and any of the $(CH_2)_n$— groups are independently optionally substituted by one or two $C_{1-4}$ alkyl groups;

B is a group of formula where $-R^1-CQ^2(OH)-C(Q^3)(Q^4)-NQ^5-R^2$, where $R^1$ is a bond or $-OC(Q^6)(Q^7)-$, $R^2$ is hydrogen or $C_{1-6}$ alkyl, and $Q^2-Q^7$ are independently hydrogen, $C_{1-4}$ alkyl, or a group of formula $-(C(Q^8)(Q^9))_xPh$, in which x is 1 or 2, Ph is a phenyl group optionally substituted by one or more groups independently selected from hydroxy, $C_{1-4}$ alkyl, and $C_{1-4}$ alkoxy, and $Q^8$ and $Q^9$ are independently hydrogen or $C_{1-4}$ alkyl;

Z is selected from carboxyl and carboxyl derivatives, e.g., esters; D is hydrogen or a saturated or unsaturated $C_{1-6}$ aliphatic substituent optionally substituted by an amino group;

$G^1$, $G^2$ and $G^3$ are independently selected from hydrogen and $C_{1-4}$ alkyl;

(X) is a mono, bi-, or tri-cyclic aromatic ring system optionally containing one or more heteroatoms; and (Y) is a mono- or bi-cyclic nitrogen-containing ring system (attached to $-CO-C(D)(G^3)-$ by said nitrogen atom) optionally containing one or more other heteroatoms and optionally substituted by one or more substituents independently selected from $C_{1-6}$ alkyl and aryl (e.g., phenyl), or (Y) is a nitrogen atom attached to E directly by a bond or indirectly by a $C_{1-4}$ alkylene moiety and also attached to a $C_{6-7}$ cycloalkyl group; in either case (Y) may optionally be linked by a $C_{3-5}$ alkylene bridge to $G^3$ or D to form a closed ring;

and physiologically acceptable salts thereof;

with the proviso that:

when in the definition of A, k and m are both 0 or both 1 and Q is a —CO— group, and, in the definition of B, $R^1$ is a group of formula $-OC(Q^6)(Q^7)-$ as hereinbefore defined and $R^2$ is a $C_{1-6}$ alkyl group;

D is hydrogen or a $C_{1-6}$ alkyl group;

(X) is a benzene ring or a naphthyl or indolyl ring system, any of which is optionally substituted in any position by one or more substituents independently selected from $C_{1-4}$ alkyl (itself optionally substituted by one or more halogen atoms), $C_{1-4}$ alkoxy, halo, nitro, amino, carboxyl, $C_{1-4}$ alkoxycarbonyl and hydroxy, then (Y) is not a pyrrolidinyl, oxazolidinyl, or thiazolidinyl ring, or a ring system selected from indolinyl, quinolinyl, and tetrahydroquinolinyl, with the further proviso that at least one of the alkyl substituents is further substituted with an —S—NO group.

The invention also relates to compounds of the Formula (XXXVI)

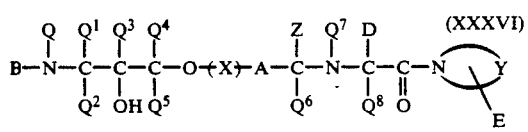

wherein Q and $Q^1$-$Q^8$ are independently selected hydrogen and $C_{1-4}$ alkyl:

A is a group of formula —$(CO)_k$—$(NQ^9)_m$—$(CH_2)_n$— where k and m are either both or both 1, n is from 1 to 6, $Q^9$ is selected from hydrogen and $C_{1-4}$ alkyl and any of the —$(CH_2)_n$— groups independently are optionally substituted by one or two $C_{1-4}$ alkyl groups;

B is a $C_{1-6}$ alkyl group;

E and Z are independently selected from carboxy and derivatives thereof;

D is hydrogen or a $C_{1-6}$ alkyl group which is optionally substituted by an amino group;

(X) is a benzene ring or a naphthyl or indolyl ring system any of which is optionally substituted in any position by one or more substituents independently selected from $C_{1-4}$ alkyl (itself optionally substituted by one or more halogen atoms), $C_{1-4}$ alkoxy, halo, nitro, amino, carboxy, $C_{1-4}$ alkoxycarbonyl and hydroxy; and —N Y is a pyrrolidinyl, oxazolidinyl or thiazolidinyl ring, or a ring system selected from indolinyl, quinolinyl and tetrahydroquinolinyl;

wherein at least one of the alkyl groups is substituted by an —S—NO group.

The invention also relates to compounds of the Formula (XXXVII) and (XXXVIII):

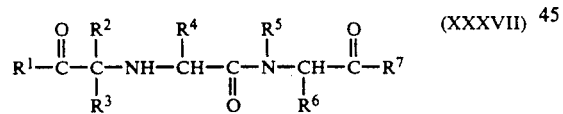

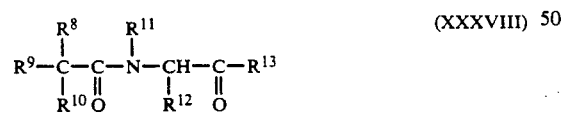

wherein at least one of $R^1$ to $R^{13}$ is substituted by —S—NO.

The invention also relates to a compound of the Formula (XXXIX):

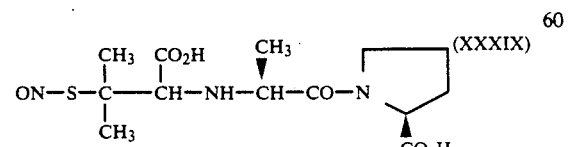

The invention also relates to a compound of the Formula (XXXX):

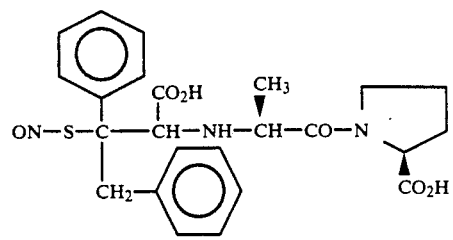

The invention also relates to a compound of the Formula (XXXXI):

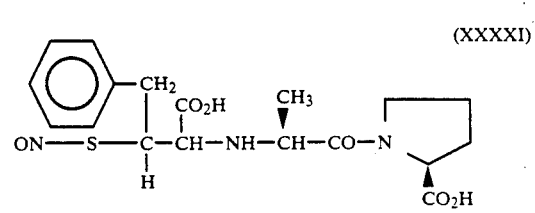

The invention also relates to a compound of the Formula (XXXXII)L

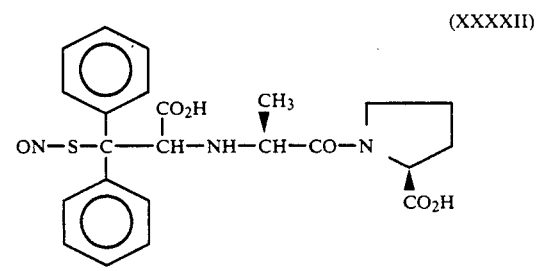

The invention also relates to a compound of the Formula (XXXXIII):

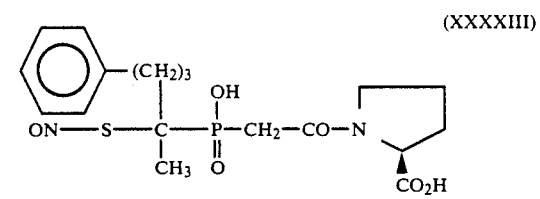

The invention also relates to a compounds of the Formula (XXXXIV):

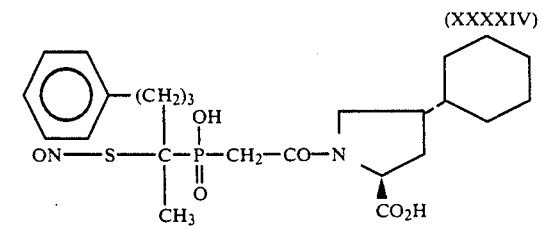

The invention also relates to a compound of the Formula (XXXXV):

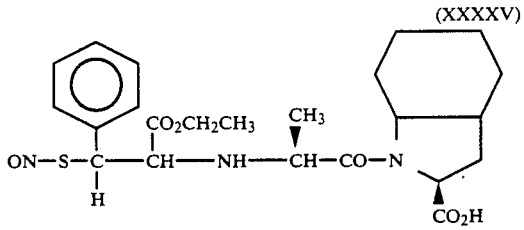

(XXXXV)

The invention also relates to a compound of the Formula (XXXXVI):

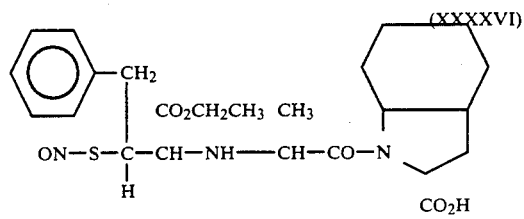

(XXXXVI)

The invention also relates to a compound of the Formula (XXXXVII):

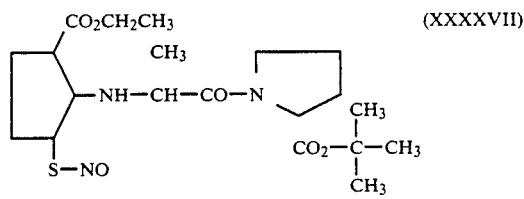

(XXXXVII)

The invention also relates to a pharmaceutical composition containing the S-nitrosothiol ACE inhibitors of the invention together with a pharmaceutically acceptable carrier.

The invention also relates to the administration of the S-nitrosothiol ACE inhibitors and the pharmaceutical compositions thereof to an animal for the treatment of various pathophysiological diseases including acute myocardial infarction, left ventricular dysfunction without overt heart failure, congestive heart failure, angina pectoris, vascular thrombosis, hypertension, Raynauds syndrome, scleroderma, toxemia of pregnancy, acute renal failure, diabetic nephropathy, renal artery stenosis, and pulmonary hypertension.

The invention also relates to methods for inhibiting ACE and effecting vasodilation and platelet inhibition by administering the pharmaceutical compositions of the invention to an animal.

Despite the report of Cushman, D. W., et al.. *Biochemistry, supra*, derivatization of the sulfhydryl group on captopril with the nitrous radical gives rise to a compound that retains the ability to inhibit ACE, and at the same time, has direct vasodilatory properties and inhibits platelet aggregation.

DESCRIPTION OF THE PREFERRED EMBODIMENTS

Figure 1:
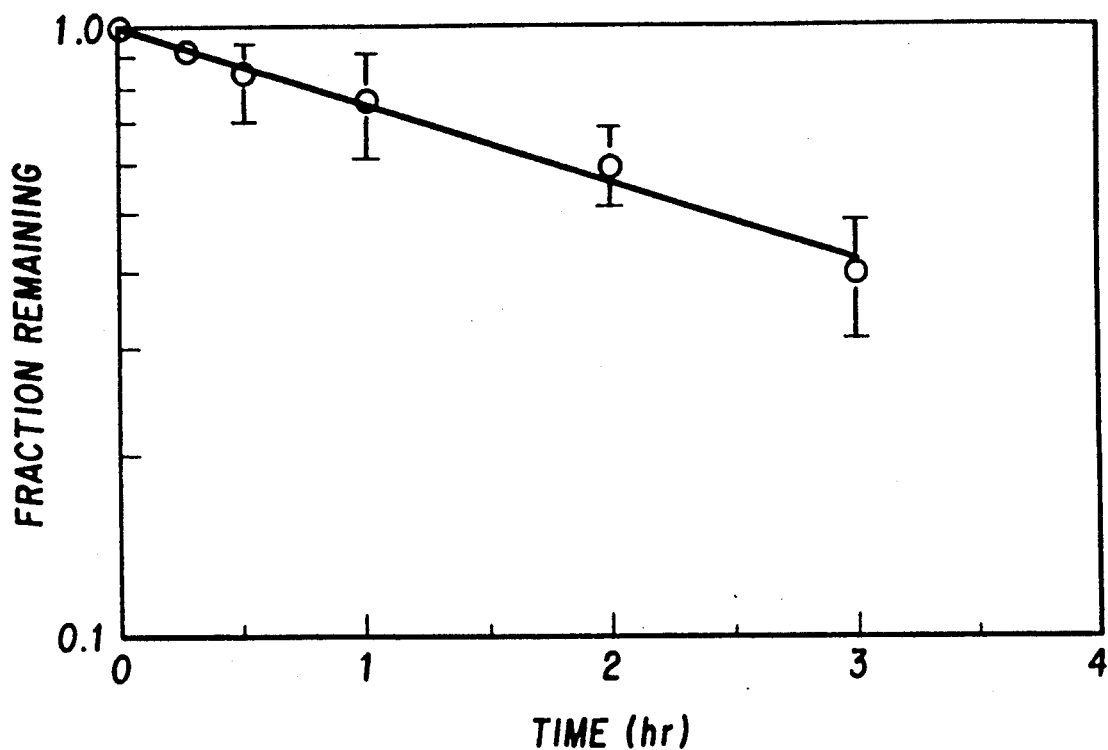
FIG. 1 depicts a graph showing the spontaneous hydrolysis of S-nitrosocaptopril in PBS. Each point represents the mean ±SEM of four experiments performed in duplicate.

The invention relates to S-nitrosothiol derivatives of ACE inhibitors. Two important properties of this class of compounds are the direct vasodilatory action and platelet inhibiting action. Although the inventors do not intend to be bound by any particular theory, the vasodilation and platelet inhibiting actions appear to be the result of the nitrosothiol moiety of the molecule. While a variety of nitrosothiols have been shown to be potent vasodilators and inhibitors of platelet aggregation (Loscalzo, J., et al.. *J. Clin. Invest.* 76:703–708 (1985)), no other compounds have been shown to be potent vasodilators and inhibitors of platelet aggregation together with the property of being an ACE inhibitor. The two mechanisms of action of the compounds of the present invention—direct vasodilation and ACE inhibition—interact synergistically to lower blood pressure.

The S-nitrosothiols of ACE inhibitors facilitate and mediate acute lowering of blood pressure on administration to animals. The longer-term effects of ACE inhibition promote lower mean blood pressures once acute administration is discontinued. The new unique properties of this class of compounds are eminently suitable for the treatment of Raynauds sundrome, scleroderma, toxemia of pregnancy, acute renal failure, diabetic nephropathy, renal artery stenosis, acute myocardial infarction, left ventricular dysfunction without overt heart failure, angina pectoris, congestive heart failure, and hypertension, in particular, pulmonary hypertension.

The compounds of the present invention also have the added benefit that they do not induce tolerance to their direct vasodilatory effect as do organic nitrates (e.g., glyceryl trinitrate) since the nitrous oxide moiety is provided as part of an active complex with a thiol group, thereby facilitating directly guanylate cyclase activation and smooth muscle relaxation. The compounds of the present invention are also relatively coronary selective, which provides an additional benefit to patients with coronary disease. Moreover, the antiplatelet effects are unique and useful in the management of unstable angina, transient ischemic attacks, and hypercoagulable states.

The S-nitroso derivatives of ACE inhibitors of the invention have the unique property of inhibiting ACE and, at the same time, causing direct vasodilation and platelet inhibition. A molecule with all three of these properties is unique. Captopril, the prototype ACE inhibitor, does not produce direct vasodilation, nor does it inhibit platelet function. Captopril does lower blood pressure, but does so solely by virtue of direct inhibition of the synthesis of angiotensin II from angiotensin I via ACE.

In particular, the invention relates to S-nitrosothiol ACE inhibitors having the formula (XXVI):

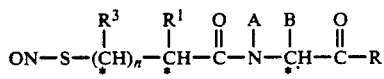

(XXVI)

wherein

R is hydroxy, $NH_2$, $NHR^4$, $NR^4R^5$ or $C_1-C_7$ alkoxy, wherein $R^4$ and $R^5$ are $C_1-C_4$ alkyl, aryl, or $C_1-C_4$ alkyl substituted by aryl;

$R^1$ is hydrogen, $C_1-C_7$ alkyl or $C_1-C_7$ alkyl substituted by phenyl, amino, guanidino, $NHR^6$ or $NR^6R^7$, wherein $R^6$ and $R^7$ are methyl, or $C_1-C_4$ acyl;

$R^3$ is hydrogen, $C_1-C_7$ alkyl or $C_1-C_7$ alkyl substituted by phenyl;

n is 0 to 2;

A is hydrogen,
lower $C_1-C_7$ alkyl,
lower $C_2-C_7$ alkylene,
lower $C_2-C_7$ alkylene substituted by hydroxy, $C_1-C_4$ alkyl, aryl, or
a $C_4-C_7$ ring which may be fused to a benzene ring;

B is hydrogen,
lower $C_1-C_7$ alkyl, phenyl,
lower $C_1-C_7$ alkyl substituted by phenyl, hydroxy, guanidino, amino, imidazolyl, indolyl, mercapto, mercapto substituted by lower $C_1-C_4$ alkyl, carbamoyl, or carboxy, or
lower $C_2-C_7$ alkylene.

Preferred nitrosothiols have the formula (XXVII):

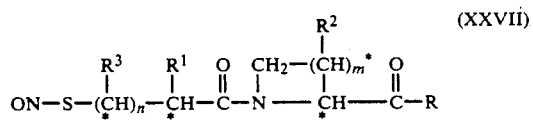

(XXVII)

wherein R, $R^1$, $R^3$ and n are as defined above; $R^2$ is hydrogen, hydroxy, $C_1-C_4$ alkoxy, aryloxy or $C_1-C_7$ alkyl; and m is 1 to 3.

The Formulae (XXVI) and (XXVII) above represents compounds having up to four asymmetric centers (represented by *). It is to be understood these compounds, and the other S-nitrosothiol ACE inhibitors of the invention, may exist in stereoisomeric, racemic, or diastereomeric forms. However, compounds derived from L-proline and its derivatives are preferred.

Preferred proline nitrosothiol derivatives of the invention include:

S-nitrosocaptopril,
N-acetyl-S-nitroso-D-cysteinyl-L-proline,
N-acetyl-S-nitroso-D,L-cysteinyl-L-proline,
1-(4-amino-2-(S-nitroso)mercaptomethylbutanoyl)-L-proline,
1-[2-(S-nitroso)mercaptomethyl-6-(N-methyl-N-acetyl-amino)
hexanoyl]-L-proline,
1-[5-guanidino-2-(S-nitroso)mercaptomethylpentanoyl]-L-proline, 1-[5-amino-2-(S-nitroso)mercaptomethylpentanoyl]-4-hydroxy-L-proline,
1-[5-guanidino-2-(S-nitroso)mercaptomethylpentanoyl]-4-hydroxy-L-proline,
1-2-aminomethyl-3-(S-nitroso)mercaptomethylpentanoyl]-L-proline,
S-nitroso-L-cysteinyl-L-proline,
and compounds of the Formulae:

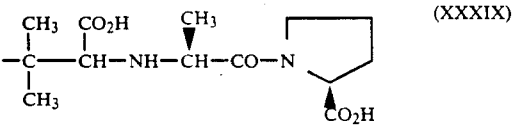

(XXXIX)

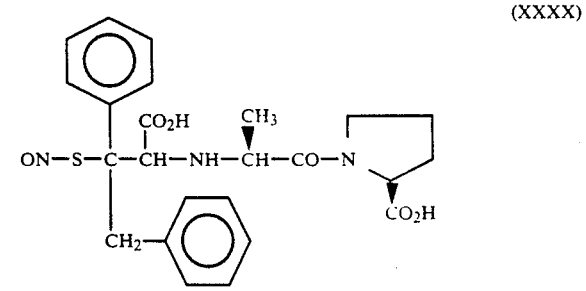

(XXXX)

-continued

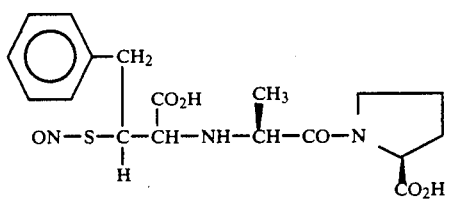
(XXXXI)

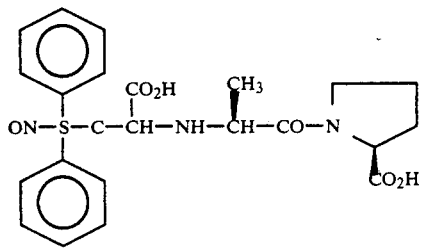
(XXXXII)

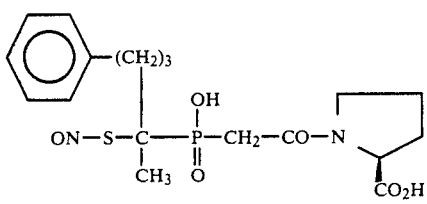
(XXXXIII)

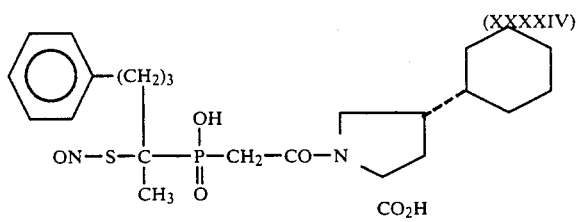
(XXXXIV)

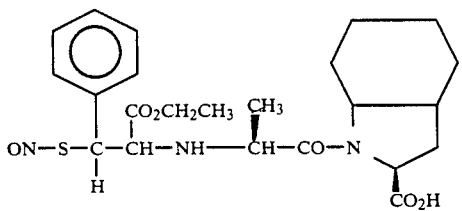
(XXXXV)

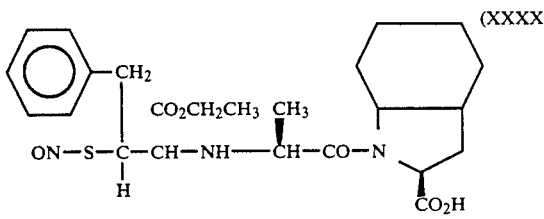
(XXXXVI)

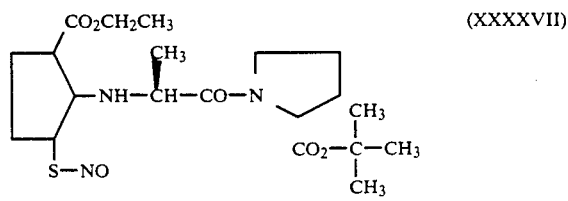
(XXXXVII)

An especially preferred proline nitrosothiol derivative is S-nitrosocaptopril.

Preferred non-proline nitrosothiol derivatives include:
N-[5-amino-2-(S-nitroso)mercaptomethylpentanoyl]glycine,
N-[5-amino-2-(S-nitroso)mercaptomethylpentanoyl]-L-leucine,
N-[5-amino-2-(S-nitroso)mercaptomethylpentanoyl]-L-phenylalanine,
N-[5-amino-2-(S-nitroso)mercaptomethylpentanoyl]-L-serine,
1-N-[5-amino-2-(S-nitroso)mercaptomethylpentanoyl]pipecolic acid,
$N^a$-[5-amino-2-(S-nitroso)mercaptomethylpentanoyl]-L-arginine,
$N^a$[5-amino-2-(S-nitroso)mercaptomethylpentanoyl]-L-lysine,
$N^a$[5-amino-2-(S-nitroso)mercaptomethylpentanoyl]-L-histidine,
N-5-amino-2-(S-nitroso)mercaptomethylpentanoyl]-L-methionine,
N-5amino-2-(S-nitroso)mercaptomethylpentanoyl]-L-tryptophan,
N-5-amino-2-(S-nitroso)mercaptomethylpentanoyl]-L-glutamine,
N-2-[5-amino-(S-nitroso)mercaptomethylpentanoyl]-L-aspartic acid,
D-(S-nitroso)cysteinyl-L-alanine,
D-(S-nitroso)cysteinyl-L-threonine,
N-5-guanidino-2-(S-nitroso)mercaptomethylpentanoyl]-L-leucine, and
1-[5-guanidino-2-(S-nitroso)mercaptomethylpentanoyl]pipecolic acid The S-nitrosothiol derivatives of ACE inhibitors may be prepared by various methods of synthesis. In general, the thiol precursor is prepared first then converted to the S-nitrosothiol derivative by nitrosylation of the thiol group with $NaNO_2$ under acidic conditions (pH = 1 to 5) gives the S-nitroso derivative. Acids which may be used for this purpose include aqueous sulfuric, acetic and hydrochloric acids.

For example, the free mercaptan precursor of the S-nitroso derivative having Formulae (XXVI) and (XXVII) may be prepared according to U.S. Pat. Nos. 4,046,889 (1977), 4,052,511, 4,053,651, 4,113,751, 4,154,840, 4,129,571 (1978), and 4,154,960 (1979) to Ondetti et al.: U.S. Pat. No. 4,626,545 (1986) to Taub; and Ryan et al., U.S. Pat. Nos. 4,692,458 (1987) and 4,692,459 (1987) to Ryan et al., incorporated herein by reference, then converted to the S-nitrosothiol derivative as described above.

For example, the compound having Formula (XXVI) may be prepared from the α-amino acyl derivative of the Formula (XXXXVIII):

(XXXXVIII)

wherein A, B and R are defined above, by acylation with an acid of the formula (XXXXIX):

(XXXXIX)

wherein n and $R^3$ have meaning defined above and $R^4$ is lower $C_1$–$C_4$ alkyl, by any of the known procedures for preparing dipeptides. For example, the carboxy group may be activated by formation of a mixed anhydride, symmetrical anhydride, acid chloride, active ester such as with N-hydroxysuccinamide and DCC, Woodward reagent K, N,N'-carbonylbisimidazole, EEDQ (N-ethoxycarbonyl-2-ethoxy-1,2-dihydroquinone) or the like. When R is lower $C_1$-$C_4$ alkoxy, this or other known methods of coupling such moieties can be used [For a review of these methods, see Methoden de Organischen Chemie (Houben-Weyl), Vol. XV, parts 1 and 2 (1974)]. The product of this reaction is a compound having the formula (L):

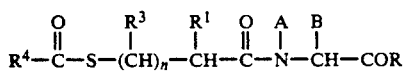
(L)

The compounds of Formula (L), wherein n is 1, may be obtained by displacement of the halo group from a carboxylic acid derivative having the formula (LII):

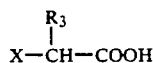
(LII)

wherein X is a halogen, preferably chlorine or bromine, with the thiol acid $R^4$—COSH, wherein $R^4$ is as defined above.

The acyl group ($R^4$—CO) of Formula (L) is then cleaved by ammonolysis to give the thiol of the formula (LIII):

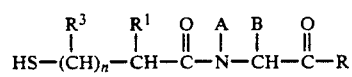
(LIII)

Nitrosylation of the thiol group with NaNO2 under acidic conditions, as described above, gives the S-nitroso derivative.

According to a preferred method of preparing S-nitroso proline derivatives of the invention, an α-amino acyl derivative of the Formula (LIV)

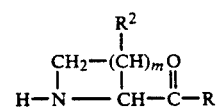
(LIV)

wherein m, $R^1$ and $R^2$ are defined above, is acylated with a haloalkanoic acid of the Formula (LV):

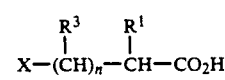
(LV)

wherein $R^1$, $R^3$ and n are defined above and X is a halogen, preferably chlorine or bromine. The amide linkage between the carboxy group of LV and the amino group of LIV may be prepared by any of the abovedescribed procedures for the preparation of dipeptides which are known to those skilled in the art. The product of this reaction is a compound of the formula (LVI):

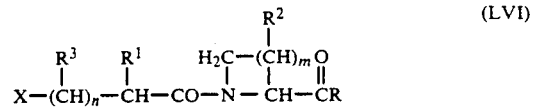
(LVI)

This product (LVI) is then subjected to a displacement reaction with a thiolacid of the general formula (LVII):

(LVII)

wherein $R^4$ is lower $C_1$-$C_4$ alkyl, under basic conditions to give a product of the general Formula (LVIII):

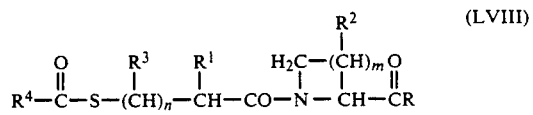
(LVIII)

This compound, in which the thiol group is protected by the acyl group $R^4$CO—, is then converted to the thiol having Formula (LIX):

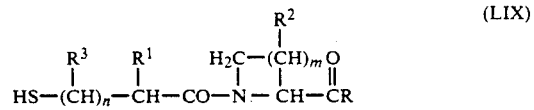
(LIX)

by ammonolysis.

It is understood that if $R^2$ is hydroxy, it may also be protected by any conventional hydroxy protecting group including, but not limited to, acyl, trialkylsilyl, dialkylarylsilyl, or tetrahydropyranyl. Nitrosylation of the thiol with NaNO2 under acidic conditions (pH=1 to 5), as described above, gives the S-nitroso derivative.

Alternatively, the compounds of Formula (XXVII) wherein n is 1 can be synthesized by addition of a thiol acid across the double bond of an acrylate derivative of the Formula (LVIII) to give Formula (LX).

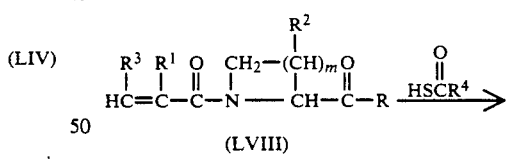
(LVIII)

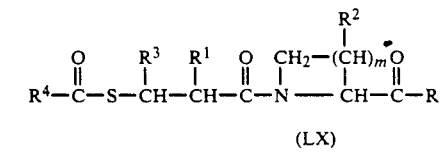
(LX)

The acyl moiety ($R^4$CO—) of Formula (LX) may then be cleaved by ammonolysis. Compounds represented by Formula (LVIII) may be obtained by acylation of the amino group of Formula (LIV) with an acrylate acid of the Formula (LXI).

(LXI)

The carboxylate group of Formula (LXI) may be activated with a conventional activating group, such as those mentioned above, before condensation with LIV.

The invention also relates to 3-[N-(2-nitrosothio-propionylamino-acetyl)]-tetrahydro-thiazolyl-4-carboxylic acid having the Formula (XXVIII):

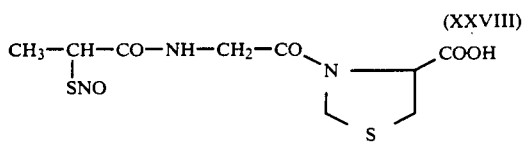

(XXVIII)

The preparation of the thiol precursor to XXVIII, 3-[N-(2-mercapto-propionyl-amino-acetyl)]-tetrahydro-thiazolyl-4-carboxylic acid (Formula (I)), is taught by Quadro, U.S. Pat. No. 4,447,419 (1984), which is incorporated by reference herein.

The invention also relates to the S-nitrosothiol derivatives of 4-phenoxy and 4-phenylthio substituted proline derivatives having Formula (XXIX):

(XXIX)

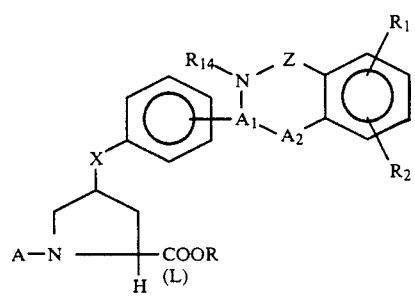
(L)

The methods for preparing the precursor to LXV (see Formula (II)) are taught by Haugwitz et al., U.S. Pat. No. 4,681,886 (1987), which is incorporated by reference herein.

The invention also relates to the S-nitrosothiol derivatives of 3,6-dihydroxyphenazine-1-carboxylic acid having the Formula (XXXI):

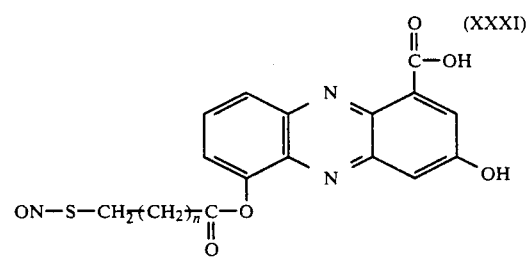

(XXXI)

Methods for preparing the precursor to XXXI (see Formula (III)) are taught by Bush et al., U.S. Pat. No. 4,568,675 (1986), which is incorporated by reference herein.

The invention also relates to S-nitrosothiol compounds of the Formula (LXVII):

$ZCHRCON(-N=CR_4R_5)CHR_6(CH_2)_nCOY$   (XXXII)

Methods for preparing the precursor to XXXII (see Formula (IV)) are taught by Bennion et al., U.S. Pat. No. 4,748,160 (1988), which is incorporated by reference herein.

The invention also relates to (S-nitrosomercapto)-1-oxoalkyl]-,1,2,3,4-tetrahydroquinoline-2-carboxylic acids having Formula (XXXIII):

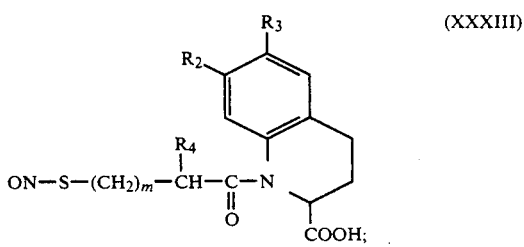

(XXXIII)

Methods for preparing the precursor to XXXIII, [(mercapto)-1oxoalkyl]-,1,2,3,4-tetrahydroquinoline-2-carboxylic acid, are taught by Portlock, U.S. Pat. No. 4,461,896 (1984), which is incorporated by reference herein.

The invention also relates to S-nitrosothiol derivatives of substituted acyl derivative of octahydro-1H-indole-2-carboxylic acid having the Formula (XXXIV):

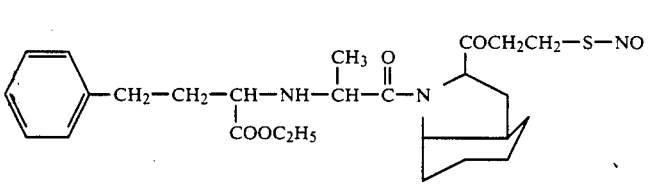

(XXXIV)

Methods for preparing the precursor to XXXIV are taught by Hoefle et al., European Patent application Publication No. 0 088 341 (1983) which is incorporated by reference herein.

The invention also relates to S-nitrosothiol derivatives having the Formula (XXXV):

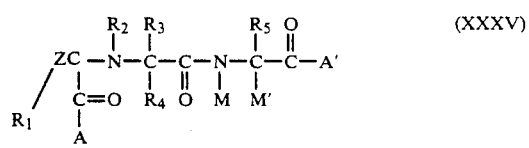

(XXXV)

Methods for preparing the precursor to XXXV (see Formula (VII)) are taught by Huange et al., U.S. Pat. No. 4,585,758 (1986), which is incorporated by reference herein.

The invention also relates to S-nitrosothiol derivatives having the Formula (XXXVI):

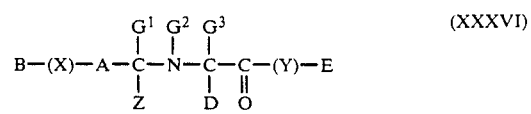

(XXXVI)

Methods for preparing the precursor to XXXVI (see Formula (VIII)) are disclosed in European Patent application Publication No. 0 237 239, which is incorporated by reference herein.

The invention also relates to S-nitrosothiol derivatives having the Formula (XXXVII):

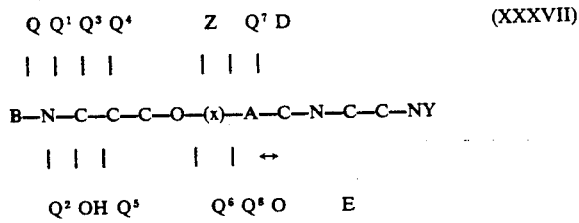

(XXXVII)

Methods for preparing the precursor to XXXVIII (see Formula (IX)) are disclosed in European Patent application Publication No. 0 174 162, published in 1986, which is incorporated by reference herein.

The invention also relates to S-nitrosothiol derivatives having the Formulae (XXXVIII) and (XXXIX):

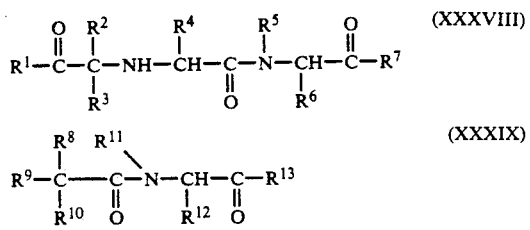

Methods for preparing the precursors to XXXVIII and XXXIX (see Formulae (X) and (XI), respectively) are disclosed in European Patent application Publication No. 0 257 485, published in 1988, which is incorporated by reference herein.

By the term "animal" is meant all animals that may experience the beneficial effects of the invention. Foremost among such animals are humans; however, the invention is not intended to be so limiting.

By the term "pharmaceutically acceptable salts" is intended compounds of the invention wherein R equals hydroxy together with a pharmaceutically acceptable base such as alkali or alkaline earth metal hydroxides, ammonium hydroxides, alkyl ammonium hydroxides, etc.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

The compositions of the present invention may be administered by any means that effect vasodilation and platelet aggregation inhibition and thereby relieve the symptoms of acute myocardial infarction, left ventricular dysfunction without overt heart failure, hypertension, pulmonary hypertension, congestive heart failure, angina pectoris, vascular thrombosis, Raynauds syndrome, scleroderma, toxemia of pregnancy, acute renal failure, diabetic nephropathy, and renal artery stenosis. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the S-nitroso compound is contained in an amount effective to achieve its intended purpose. While individual needs vary, determination of optimal ranges of effective amounts of each component is within the skill of the art. Typical dosage forms contain 1 pmole/kg to 10 mmole/kg animal of the S-nitrosothiol derivative, or an equivalent amount of the pharmaceutically acceptable salt thereof.

Administration of the compounds of the invention, for example, S-nitrosocaptopril, is desirably effected in from 1 mcg to 300 mg dosage units daily, depending on the mode of administration, preferably by oral or intravenous administration. The compounds may be administered from 1 to 4 times daily or by continuous intravenous infusion.

In addition to the pharmacologically active compounds, the new pharmaceutical preparations may contain suitable pharmaceutically facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 5 percent, preferably from about 0.1 to 0.5 percent of active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch, paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethylstarch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric Juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

EXAMPLE 1

Preparation and Characterization of S-Nitrosocaptopril

Typical preparation of S-nitrosocaptopril involve the reaction of 50 mM captopril with 50 mM $NaNO_2$ in 0.1 N acetic or sulfuric acid at room temperature for five minutes, after which the reaction solution is passed over a cation exchange resin, e.g., Dowex 50 in the protonated form, and the product eluted with water. The fractions that give positive reactions with N-(1-naphthyl)ethylenediamine, after exposure to 0.15% $HgCl_2$ and diazotization with sulfanilamide, are lyophilized. Hygroscopic, bright red crystals (m.p. 98–104° C.) were obtained that were shown to be S-nitrosocaptopril by NMR in deuterated DMSO and by mass spectroscopy.

Ultraviolet and visible absorption spectral analysis revealed five absorption maxima: 333 nm (E=1890 $M^{-1}cm^{-1}$); 404 nm (E=339 $M^{-1}cm^{-1}$); 512 nm (s) (E=7.9 $M^{-1}cm^{-1}$); and 545 nm (E=13.3 $M^{-1}cm^{-1}$). Infrared spectral analysis showed the presence of two absorption bands corresponding to the S-N bond (1152 $cm^{-1}$ and 1171 $cm^{-1}$), as well as absorption bands corresponding to the N-O bond (1428–1589 $cm^{-1}$). The proton NMR spectrum of S-nitrosocaptopril in deuterated chloroform showed a loss of the triplet absorption band at 1.55–1.6 ppm corresponding to the sulfur proton of captopril.

Analysis of the molecular weight of S-nitrosocaptopril by fast atom bombardment mass spectrometry yielded a value of 433. Unfortunately, under the oxidative conditions of atom bombardment, the rose-colored S-nitrosocaptopril underwent a color change to light yellow during disulfite-linked dimerization, thus producing dicaptopril with the predicted molecular weight of 433.

The half-life of the S-nitroso bond of S-nitrosocaptopril in physiologic buffer and in plasma was determined by incubating purified S-nitrosocaptopril in aerated PSS or in PPP, the results of which are shown in FIG. 1. Thiol-bound, mercurous-displaceable nitrite decayed monoexponentially in PSS with an estimated half-life of approximately 2.8 hours at 37° C. S-nitrosocaptopril also decays monoexponentially in PPP (data not shown) at room temperature with a similar estimated half-life (2.5 hours).

EXAMPLE 2

The Effect of S-Nitrosocaptopril on Arterial Tone

Blood Vessel Preparation. Bovine coronary or femoral arteries were obtained from an abattoir immediately after sacrifice of two- to four-week old calves. Immediately after removal, the vessel was placed in ice-cold physiologic salt solution (PSS) containing 118.3 mM NaCl, 4.7 mM KCl, 2.5 mM $CaCl_2$, 1.2 mM $MgSO_4$, 1.2 mM $KH_2PO_4$, 25.0 mM $NaHCO_3$, 11.1 mM glucose, and 0.026 mM calcium disodium (ethylenedinitrilo)-tetraacetate. The vessels were then cleaned of adventitial tissue and cut into rings of approximately 5 mm lengths. When called for by the protocol, endothelium was removed from a ring by gently rubbing the luminal surface with a watchmaker's forceps. Vascular rings with intact endothelium were then suspended in organ chambers containing 25 ml of PSS at 37° C. aerated with 95% $O_2$–5% $CO_2$. The rings were connected to force transducers (Grass FT03C, Quincy, Mass.) and changes in isometric force recorded continuously (Grass Polygraph Model 79B) over a period of 9D minutes. The optimal length-tension relationship was determined for each ring by observing the response to $10^{-6}$ M norepinephrine after increments in tension of 0.5 gm. The functional integrity of the endothelium was assessed by contracting the vessel with $10^{-6}$M norepinephrine and then observing the response to $3\times10^{-7}$M acetylcholine chloride. Vascular rings that did not relax with acetylcholine chloride were assumed to be denuded of endothelium.

Figure 2:
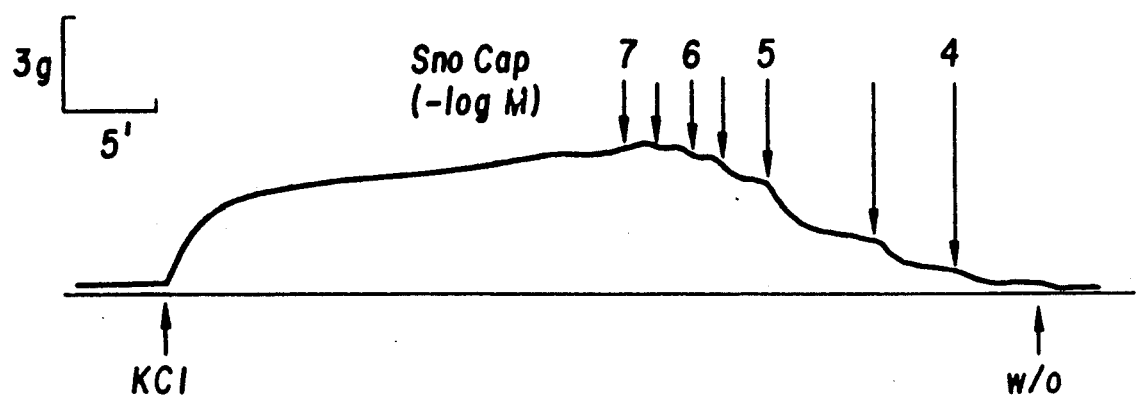
FIG. 2 depicts a graph showing the effect of S-nitrosocaptopril on the contraction of bovine femoral arteries to ncrepinephrine. S-nitrosocaptopril, but not captopril, induced dose-dependant relaxation.

Vascular ring segments with intact endothelium were maximally contracted with a concentration of norepinephrine inducing a halfmaximal response. After a stable contraction had been achieved, the tissue was exposed to increasing concentrations of S-nitrosocaptopril in cumulative half-log increments. As shown in FIG. 2, progressive relaxation was observed; captopril produced no relaxation response over the same range of concentrations. The apparent $IC_{50}$ is approximately 1 $\mu$M. This value is approximately one order of magnitude weaker than that of another model S-nitrosothiol vasodilator, S-nitroso-N-acetylpenicillamine (Ignarro et al., *J. Pharm. Exp. Therap.* 218:739-749 (1981)), in the bovine coronary artery.

EXAMPLE 3

Demonstration of the Relative Coronary Selectivity of S-Nitrosocaptopril

Bovine coronary arteries exhibited weak responses to norepinephrine. Thus, to study vasodilating agents in this tissue the vessels were first contracted with potassium chloride (40 mM). Relaxations are expressed as a percent of the concentration to 40 mM potassium chloride.

Figure 3:
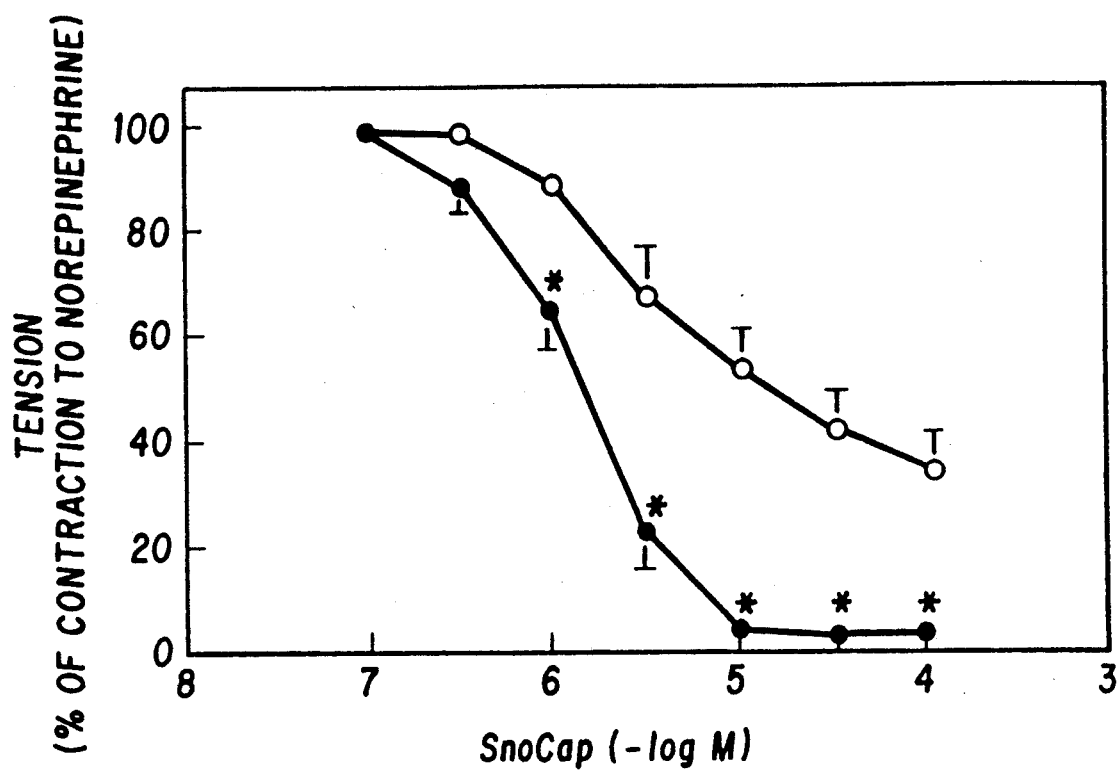
FIG. 3 depicts a graph showing the relaxation effect of S-nitrosocaptopril on the bovine coronary ● and femoral ○ arteries. *Denotes relaxation of S-nitrosocaptopril in the coronary artery which are significantly greater than those in the femoral artery ($p<0.05$). The data are expressed as a percentage of the initial tension generated by potassium chloride ($4\times10^{-2}$M; coronary arteries) or norepin. ephrine (ED$_{50}$ dose; femoral arteries), and are shown as mean ±SEM in each group (n=12).
Figure 4A:
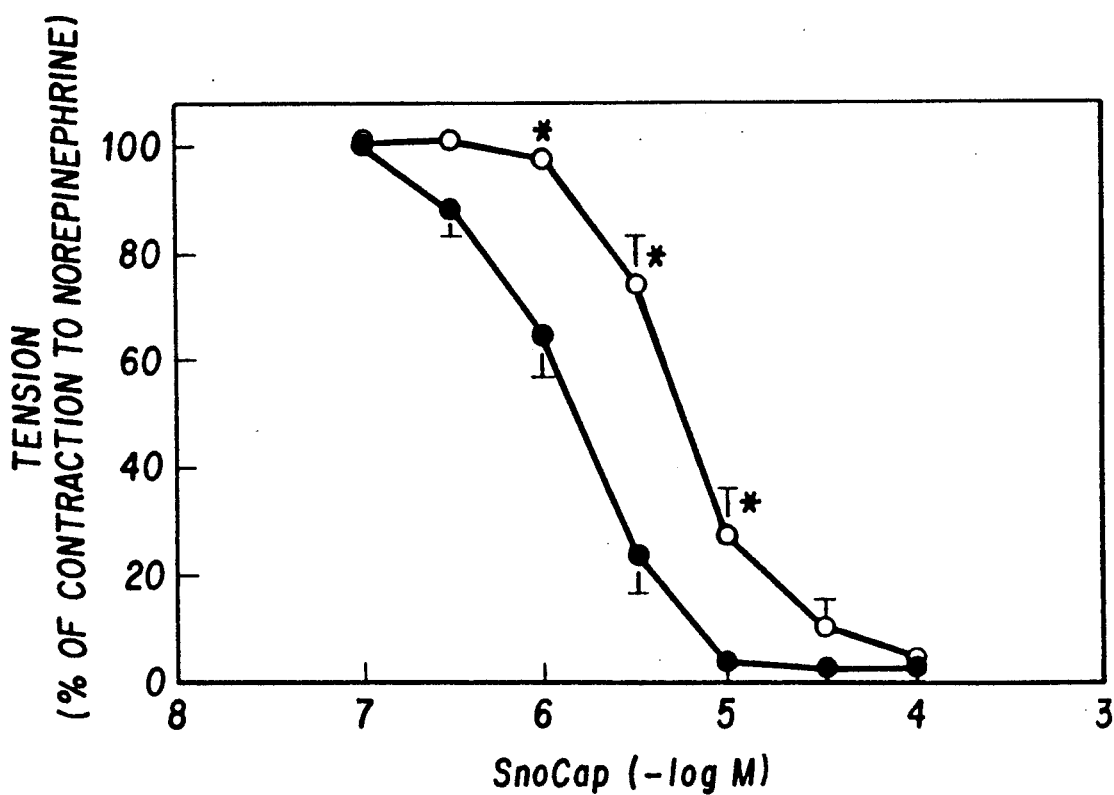
FIG. 4 depicts a graph showing the effect of S-nitrosocaptopril in a) the bovine coronary artery, and b) the bovine femoral artery in the presence (○) or absence ● of methylene blue ($10^{-5}$M) *Denotes relaxation in the presence of methylene blue which are significantly less than control ($p<0.05$). The data are expressed as a percentage of the initial tension generated by potassium chloride ($4\times10^{-2}$M; coronary arteries) or norepinephrine (ED50 dose; femoral arteries), and are shown as mean ±SEM in each group (n=12).
Figure 4B:
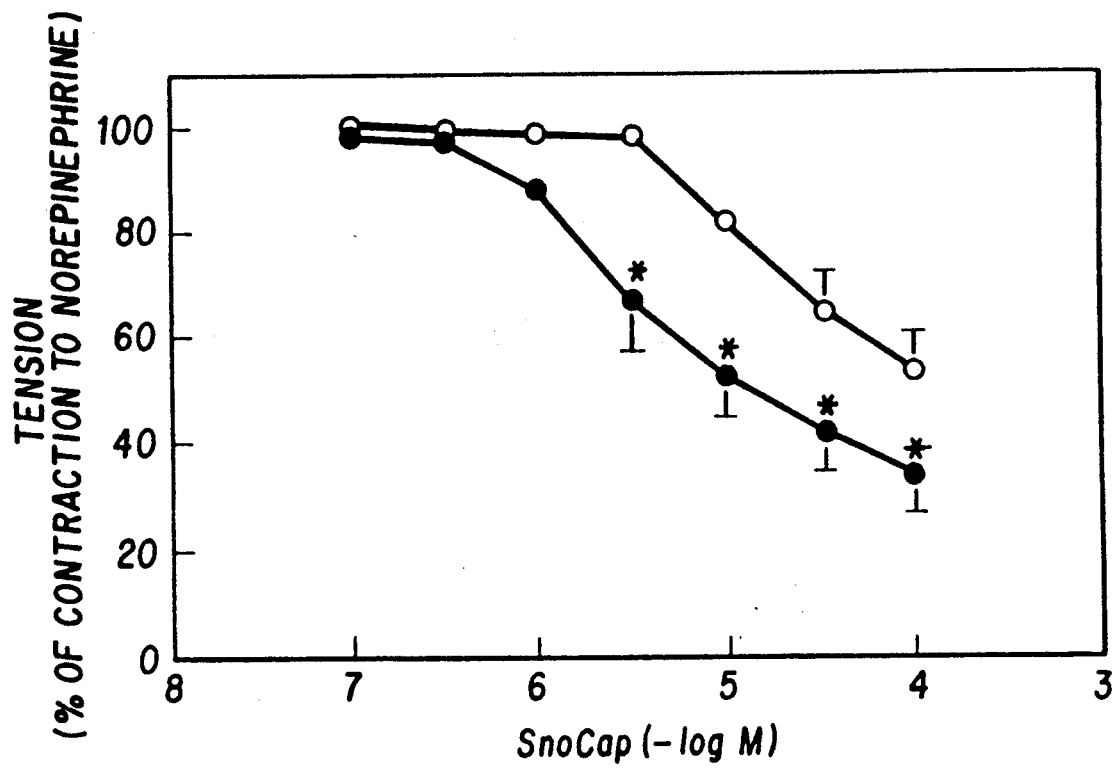
Figure 5:
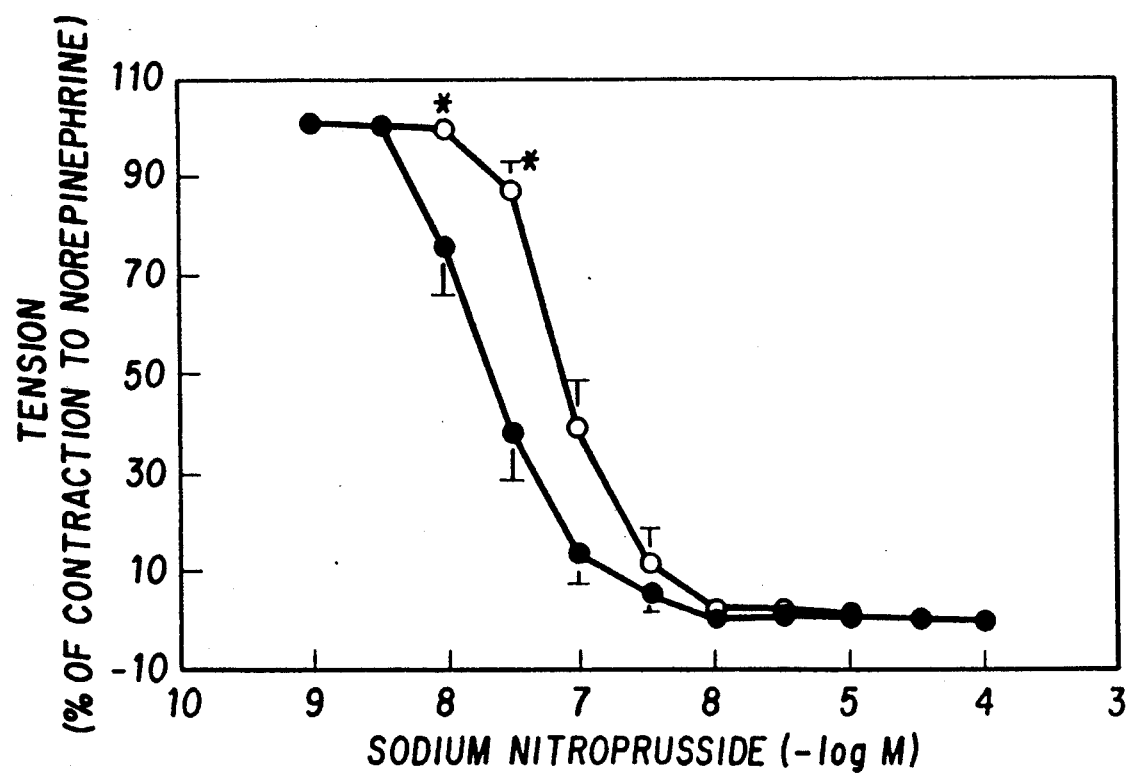
FIG. 5 depicts a graph showing the relaxation to sodium nitroprusside in the bovine coronary artery in the presence ○; n=7) or absence ●; n=12) of a subthreshhold dose of S-nitrosocaptopril. The data are expressed as a percentage of the initial tension generated by potassium chloride ($4\times10^{-2}$M; coronary arteries) and are shown as mean ±SEM in each group.

In the bovine coronary artery the optimal length-tension relationship was achieved at $5.7 \pm 1.9$ g (n=12); in these tissues, potassium chloride (40 mM) induced a stable contraction of $7.3 \pm 4.3$ g. S-nitrosocaptopril attenuated these contractions in a dose-dependent manner with an $IC_{50}$ of $1.9 \pm 0.2 \times 10^{-6}$M and a maximal relaxation of $97 \pm 7\%$. The maximum inhibitory effect of S-nitrosocaptopril was significantly greater in the coronary artery than in the femoral artery (FIG. 3). The $IC_{50}$ of S-nitrosocaptopril in the coronary artery was significantly less than that in the femoral artery ($1.9 \pm 0.2 \times 10^{-6}$M vs. $5.6 \pm 0.3 \times 10^{-6}$M, respectively, $p<0.05$, n=6). Relaxations to S-nitrosocaptopril were inhibited by the antagonist of soluble guanylate cyclase, methylene blue (FIG. 4). Sodium nitroprusside induced dose-dependent relaxations of contractions to potassium chloride. The relaxation to sodium nitroprusside was inhibited by subthreshold doses of S-nitrosocaptopril (FIG. 5).

EXAMPLE 4

The ACE Inhibitino Effect of S-Nitrosocaptopril in Canine Femoral Arteries

Figure 6:
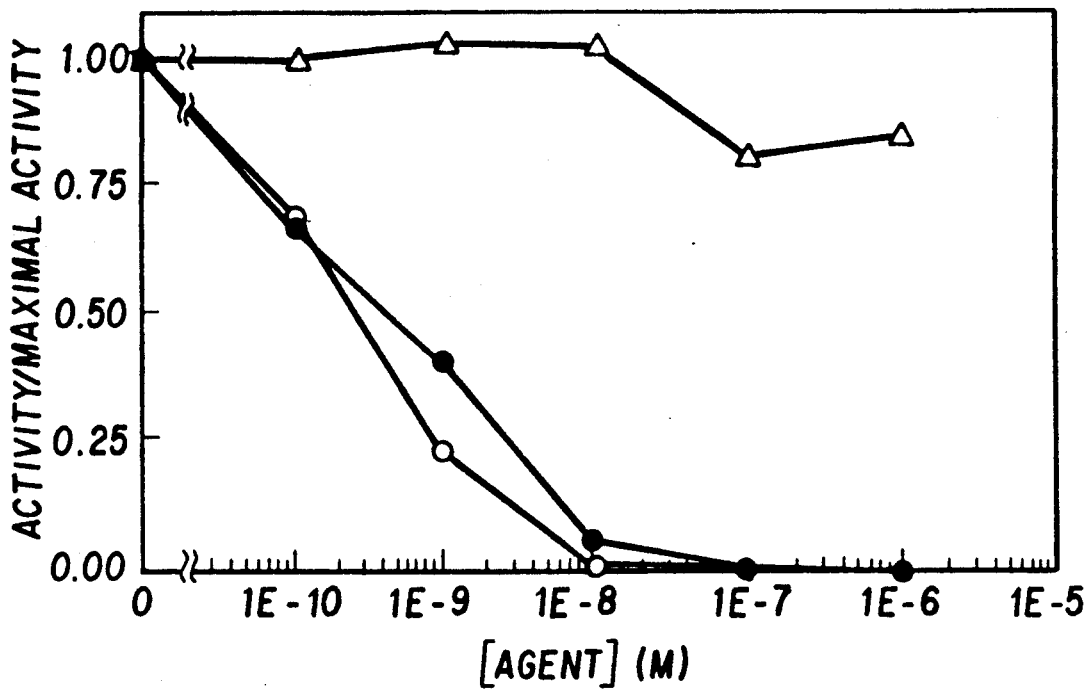
FIG. 6 depicts a graph showing the effect of S-nitrosocaptopril on ACE inhibition. The concentrations of S-nitrosocaptopril ○; and captopril ● ranged from $10^{-10}$ to $10^{-8}$ and produced almost complete inhibition of ACE. Vehicle (Δ) had almost no effect on ACE activity.

In order to examine the ACE inhibiting properties of S-nitrosocaptopril, increasing concentrations of S-nitrosocaptopril or captopril were added to the suspensions of a rat lung source of ACE (according to Friedland and Silverstein, *Am J. Clin. Pathol.* 66:416423 (1976)) and the extent of inhibition determined. Under the conditions of this assay (0.1 M potassium phosphate, pH 8.3, 0.3 M NaCl at 37° C.), ACE preparations generated 6.32 nmoles of product/mg protein/min. Concentrations of S-nitrosocaptopril ranging from $10^{-7}$-$10^{-5}$M produced 98-100% inhibition of this activity, values that were identical for the same concentrations of captopril itself (FIG. 6).

EXAMPLE 5

The Inhibitory Effect of S-Nitrosocaptopril on Platelet Aggregation Induced by ADP Platelets. Volunteers who had not ingested acetylsalicylic acid for at least ten days provided venous blood within one hour of use. Blood was anticoagulated with 13 mM trisodium citrate and the platelet-rich plasma (PRP) prepared from it by centrifugation at 160 g for ten minutes. Platelet counts were determined using a Coulter counter (Model ZM; Coulter Electronics, Hialeah, Fla.) and adjusted with platelet-poor plasma (PPP) to $1.5 \times 10^8$ platelets/ml prior to use.

Platelet Aggregation. Platelet aggregation was monitored using a standard nephelometric technique (Born and Cross, *J. Physiol* (London) 168:178-195 (1963)) in which PRP was incubated at 37° C. with a final concentration of 11 µM ADP and stirred at 900 rpm in a Payton dual channel aggregometer (Payton Associates, Inc., Buffalo, N.Y.). Aggregation was quantitated by measuring either the maximal rate of change of light transmittance or the extent of change of light transmittance.

Figure 7:
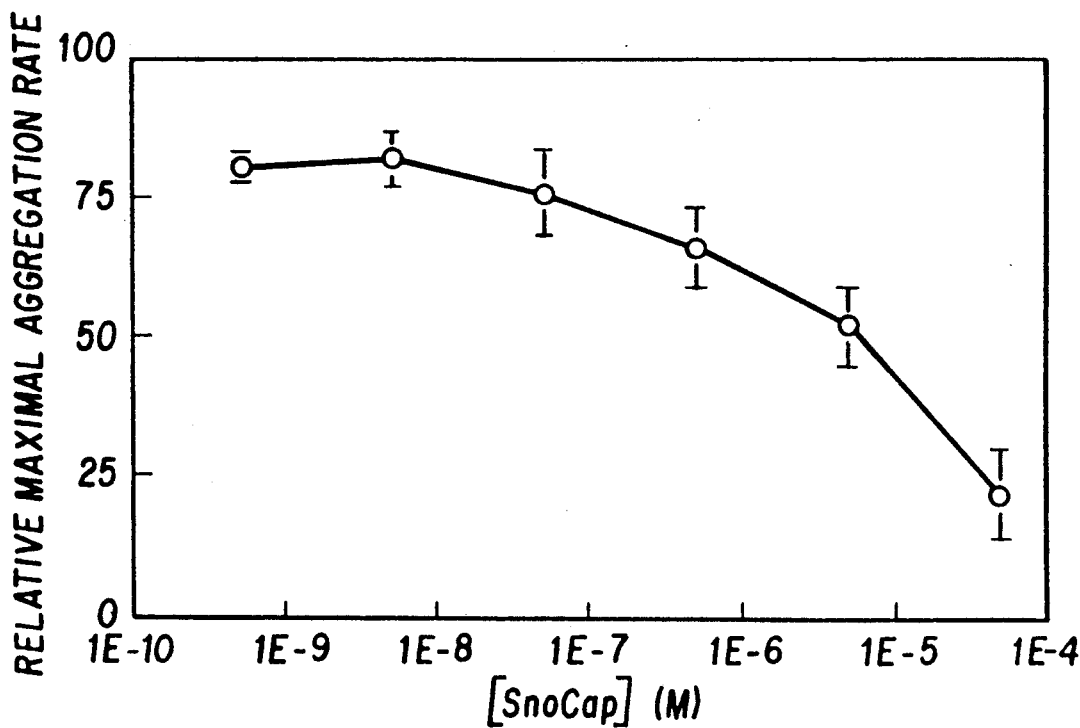
FIG. 7 depicts a graph showing the effect of S-nitrosocaptopril on platelet aggregation. Platelets in PRP were incubated with S-nitrosocaptopril over a range of concentrations for three minutes, after which ADP was added to a final concentration of 11 uM. The maximal rate of aggregation was measured and plotted as a percentage of that observed in the absence of S-nitrosocaptopril. Each point represents the mean ±SEM of five experiments each performed in duplicate.

The effect of S-nitrosocaptopril on platelet aggregation was examined by incubating platelets in PRP with increasing concentrations of S-nitrosocaptopril for four minutes, after which aggregation was induced with 11 µM ADP. Maximal rates of aggregation were measured and plotted as a fraction of that in the absence of S-nitrosocaptopril (FIG. 7) The results show that S-nitrosocaptopril inhibits platelet aggregation in PRP to 11 µM ADP with an $IC_{50}$ of approximately 80 µM, while captopril has no inhibitory effect.

EXAMPLE 6

Figure 8:
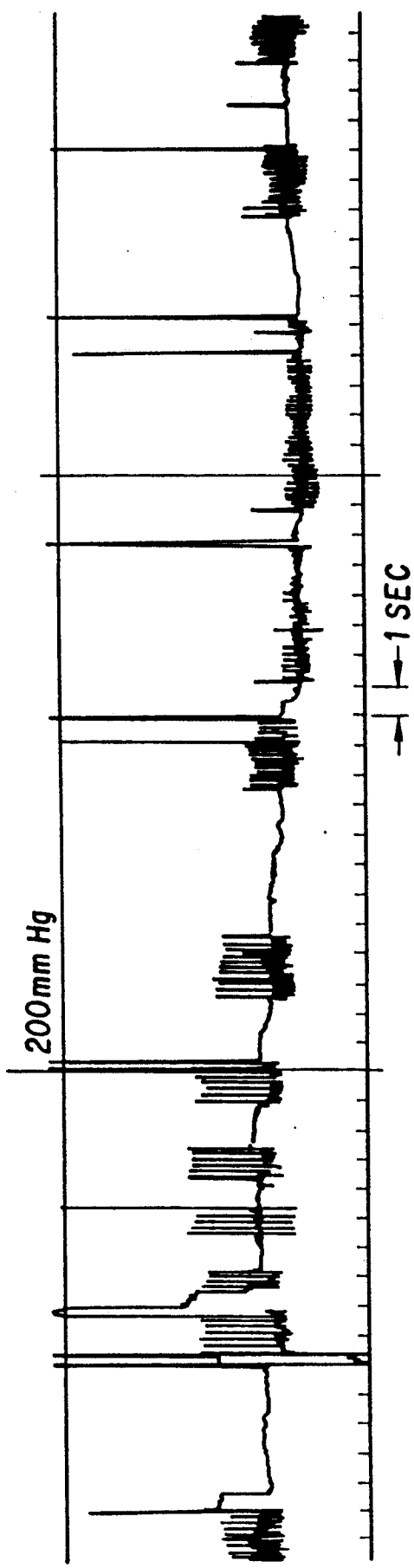
FIG. 8 depicts a strip chart record showing the effect on blood pressure of anesthetized rabbits treated with S-nitrosocaptopril.

The Acute Effect of S-Nitrosocaptopril on Arterial Pressure in the Anesthetized Rabbit A 1 mM solution of S-nitrosocaptopril was infused in an ear vein of the rabbit at rates from 0.02 to 2.2 ml/min and the phasic and mean arterial pressure recorded in the femoral artery. As shown in FIG. 8, a clear decrease in blood pressure occurred upon administration of S-nitrosocaptopril. Solutions of captopril and $NaNO_2$ at the same concentration, and infused at the same rate, had no effect on blood pressure.

EXAMPLE 7

The Effect of S-nitrosocaptopril on Vascular and Platelet cGMP Levels

Since the postulated mechanism by which the nitrosothiol moiety of S-nitrosocaptopril directly relaxes vascular smooth muscle and attenuates the platelet aggregation response is believed to be through activation of soluble guanylate cyclase, cGMP (and cAMP) levels were measured in vessel ring segments and in platelets incubated with $10^{-5}$M S-nitrosocaptopril. After incubation for one minute, cGMP levels increased 36.5-fold in vascular rings from D.001 pmol/mg tissue to 0.0375 pmol/mg tissue; after incubation for one minute, cGMP levels increased 11.3-fold in platelets from 0.48 pmoles/$10^8$ platelets to 5.44 pmoles/$10^8$ platelets. Under the same incubation conditions, cAMP levels did not change from basal levels in vessel rings or platelets.

EXAMPLE 8

Inhibition of Converting Enzyme by S-nitrosocaptopril

In the bovine femoral artery, angiotensin I induced dose-dependent contractions with a maximum response of $4.4 \pm 1.6$ g and an average $ED_{50}$ value of $8.1 \pm 0.5 \times 10^{-9}$Mm (n=11). Similarly, angiotensin II induced dose-dependent contractions with a maximum response of $6.4 \pm 2.5$ g and an average $ED_{50}$ value of $8.3 \pm 3.2 \times 10^{-9}$M (n=6). The competitive inhibitor of angiotensin II, saralasin ($10^{-7}$M), attenuated contractions to angiotensin I and angiotensin II (Table I). Saralasin ($10^{-8}$M) inhibited contractions to angiotensin I but not those to angiotensin II. Lower concentrations of saralasin had no effect on either agonist. Therefore, contractions to angiotensin I appear to be due to its conversion to angiotensin II in the bovine femoral artery, as they are potently inhibited by the specific AII antagonist saralasin.

Figure 9:
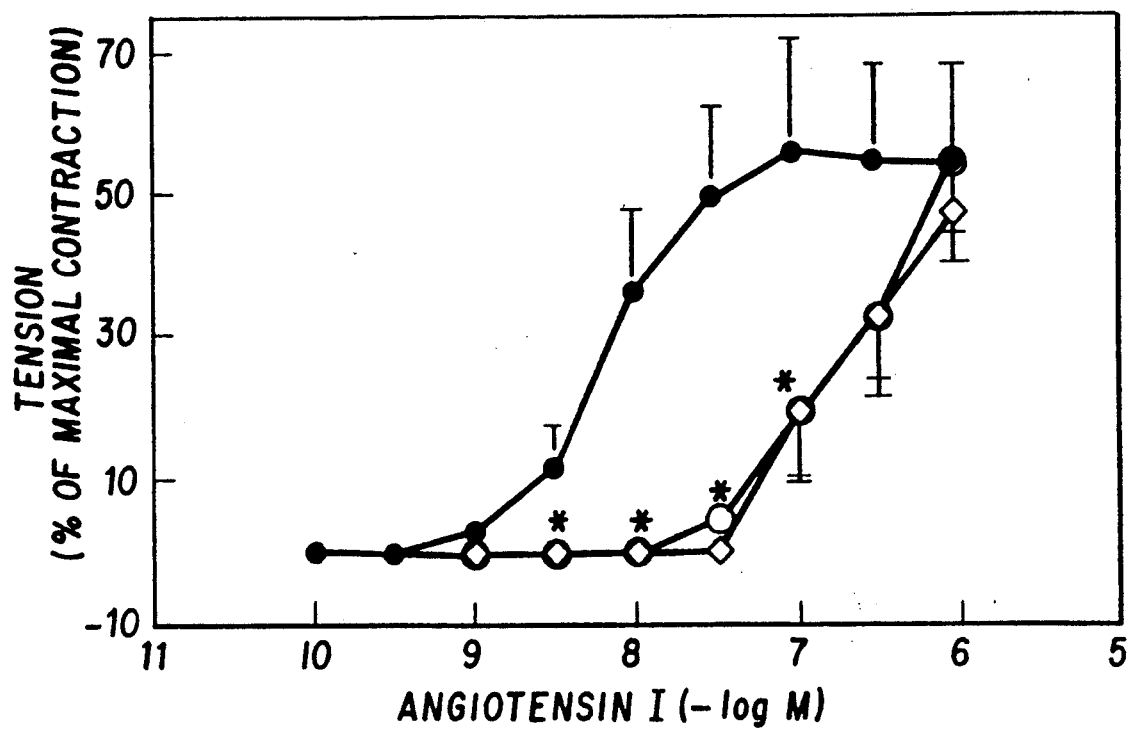
FIG. 9 depicts a graph showing the contraction of the bovine femoral artery to angiotensin I after incubation with captopril ($10^{-6}$; ◊), S-nitrosocaptopril ($10^{-6}$ M; o), or vehicle control (●). The data are expressed as a percentage of the maximal response to norepinephrine ($10^{-6}$M) and are shown as mean ±SEM in each group (n=7).
Figure 10:
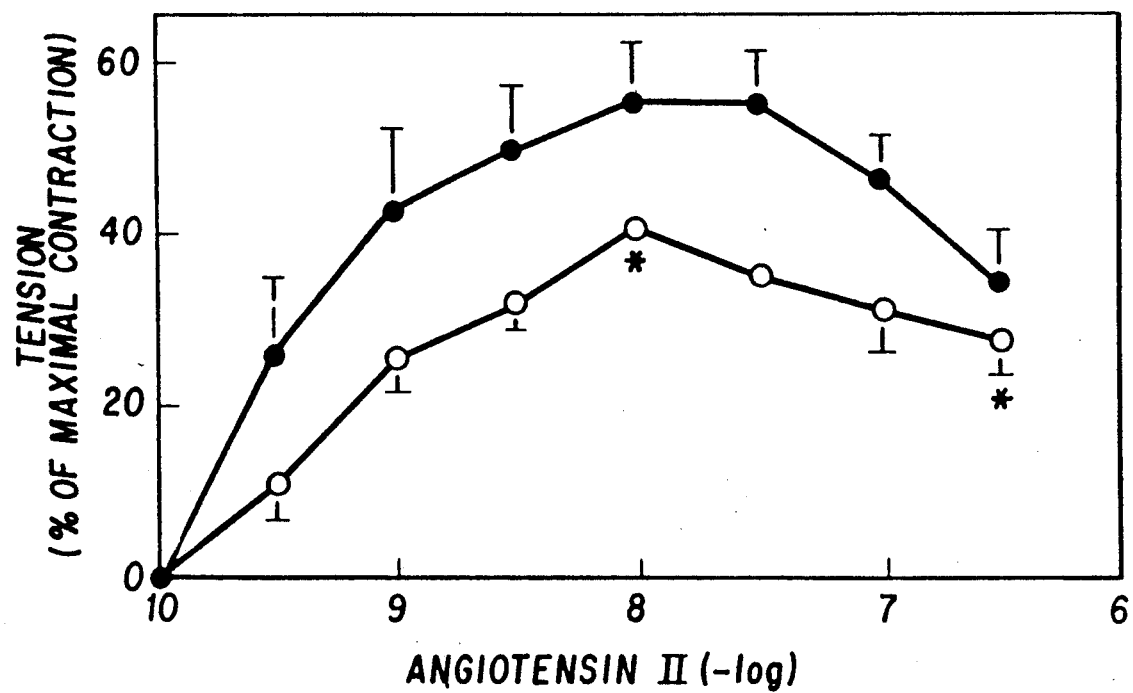
FIG. 10 depicts a graph showing the contraction of the bovine femoral artery to angiotensin II in the presence (○) or absence (●) of S-nitrosocaptopril ($10^{-6}$ M). *Denotes responses to angiotensin II in the presence of S-nitrosocaptopril are significantly less than control. The data are expressed as a percentage of the maximal response to norepinephrine ($10^{-4}$M) and are shown as mean ±SEM in each group (n=6).

S-nitrosocaptopril ($10^{-6}$M) and captopril ($10^{-6}$M) caused identical parallel shifts in the response to angiotensin I (log shifts at the $ED_{50}$ of $1.74 \pm 0.25$ (56-fold;

p<0.001) and 1.71±0.20 (51-fold; p<0.001, respectively, n=6, FIG. 9). S-nitrosocaptopril ($10^{-6}$M) also attenuated the maximum response to angiotensin II (55.8±6.9% vs. 41.0±2.6% of the maximal response to norepinephrine, n=5, p<0.05; FIG. 10).

In the bovine femoral artery contracted with a concentration of norepinephrine inducing a half-maximal response, bradykinin induced a biphasic response. At lower concentrations, bradykinin caused relaxations that were abolished by removal of the endothelium. At higher concentrations, bradykinin caused an increase in tension which was not affected by removal of the endothelium. Neither response to bradykinin was affected by captopril ($10^{-6}$M) or S-nitrosocaptopril ($10^{-6}$M).

Thus, S-nitrosocaptopril and captopril equally inhibited contractions to angiotensin 1. Undoubtedly, some of the effect of S-nitrosocaptopril upon contraction to angiotensin I must be attributable to activation of guanylate cyclase. In comparison to its effect on angiotensin II (5-fold shift rightward in the dose response curve), S-nitrosocaptopril induces a greater shift (50-fold) in the response to angiotensin I. This suggests that both inhibition of converting enzyme and direct vasodilation accompanied by activation of soluble guanylate cyclase play a role in the action of S-nitrosocaptopril against angiotensins.

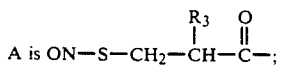

R is selected from hydrogen, lower ($C_1$-$C_4$) alkyl, benzyl, benzhydryl, and salt forming ion;

$R_1$ and $R_2$ are independently selected from hydrogen, halogen, lower alkyl, lower alkoxy, halo substituted lower alkyl, nitro, and —$SO_2NH_2$;

Z id

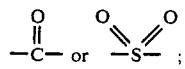

$R_3$ is hydrogen, lower alkyl, halo substituted lower alkyl, phenyl, benzyl, phenethyl, or cycloalkyl;

$R_{14}$ is hydrogen, lower alkyl, cycloalkyl-$(CH_2)_n$-, wherein n is one, two, three or four;

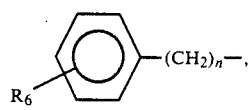

TABLE I

Effect of Saralasin on contractions to Angiotensin I or Angiotensin II in the Bovine Femoral Artery (n = 6)

| Agonist | Antagonist | Contraction to Agonist ($-\log M$)[a] | | | | | | |
|---|---|---|---|---|---|---|---|---|
| | | 9 | 8.5 | 8 | 7.5 | 7 | 6.5 | 6 |
| Angiotensin I | Sar 0 (control) | 0 | 3.3 ± 5.9 | 12.6 ± 11.4 | 27.7 ± 12.7 | 38.6 ± 15.9 | 42.5 ± 13.4 | 45.3 ± 13.5 |
| | Sar $10^{-9}$ M | 0 | 0 | 3.9 ± 1.5 | 22.6 ± 10.1 | 33.0 ± 12.6 | 31.4 ± 10.7 | 25.6 ± 13.0 |
| | Sar $10^{-8}$ M | 0 | 1.6 ± 1.6 | 7.9 ± 7.9 | 16.3 ± 9.4* | 19.6 ± 7.0* | 35.7 ± 22.1 | 35.5 ± 7.0 |
| | Sar $10^{-7}$ M | 0 | 0 | 0* | 0* | 0* | 0* | 0.9 ± 0.9* |
| Angiotensin II | Sar 0 (control) | 0 | 11.8 ± 1.1 | 28.8 ± 1.7 | 40.3 ± 2.6 | 47.2 ± 2.9 | 57.1 ± 3.1 | 57.9 ± 3.1 |
| | Sar $10^{-9}$ M | 2.4 ± 1.2 | 18.5 ± 9.6 | 34.0 ± 12.9 | 43.4 ± 16.9 | 51.8 ± 18.8 | 51.8 ± 18.8 | 51.8 ± 18.8 |
| | Sar $10^{-8}$ M | 0 | 0.9 ± 0.9 | 10.7 ± 8.1 | 24.0 ± 13.8 | 32.4 ± 17.3 | 32.8 ± 20.4 | 32.8 ± 21.0 |
| | Sar $10^{-7}$ M | 0 | 0 | 1.7 ± 1.7* | 2.8 ± 2.8* | 3.2 ± 1.8* | 9.2 ± 5.3* | 6.0 ± 3.0* |

[a]Contractions are expressed as a percentage of the maximal contraction to norepinephrine ($10^{-4}$ M).
[b]Vascular rings were incubated in parellel with these concentrations of saralasin for 45 minutes prior to the addition of agonists to the bath.
*Difference between control and treated rings is statistically significant (p < 0.05).

What is claimed is:

1. A pharmaceutically acceptable S-nitrosothiol having the formula:

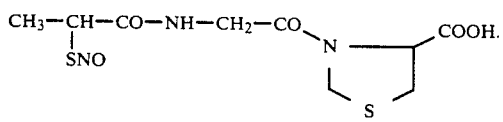

2. A pharmaceutically acceptable S-nitrosothiol having the formula:

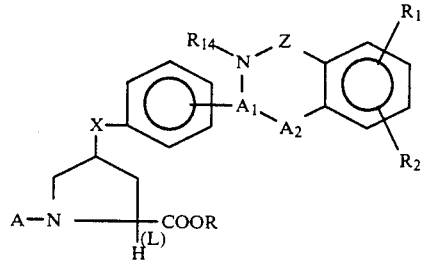

wherein
X is oxygen or sulfur;
—$A_1$—$A_2$— is —CH—NH or —C=N—;

halo substituted lower alkyl, hydroxy substituted lower alkyl, —$(CH_2)_q$—N(lower alkyl)$_2$, or —$(CH_2)_q$—$NH_2$, wherein q is one, two, three or four; and $R_6$ is hydrogen, lower alkyl, lower alkoxy, halogen, or hydroxy.

3. A pharmaceutically acceptable S-nitrosothiol selected from the group of the following formulae:

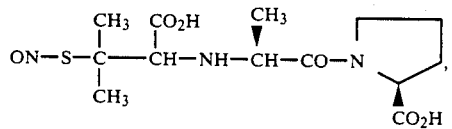

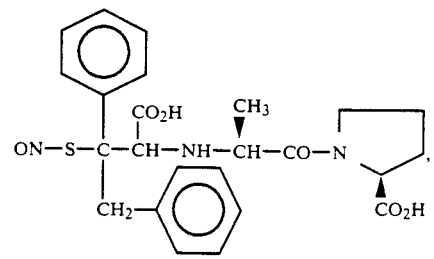

-continued

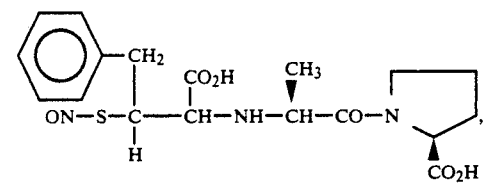

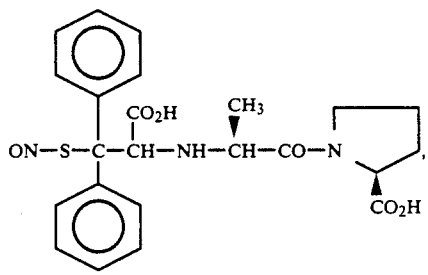

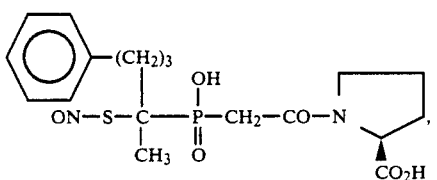

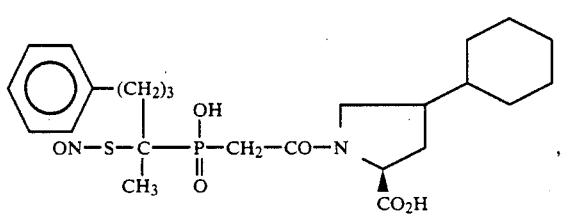

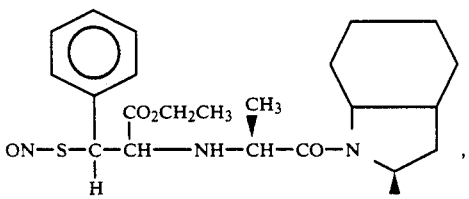

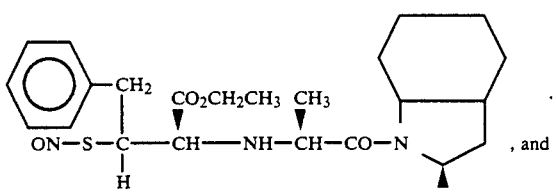

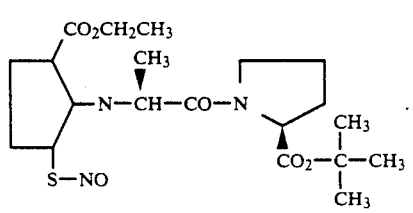

4. A pharmaceutical composition comprising the S-nitrosothiol of any of claims 1-3, and a pharmaceutically acceptable carrier.

5. A method for treating a cardiovascular-renal disease, comprising administering an effective amount of the S-nitrosothiol of any one of claims 1-3 to an animal in need of such treatment.

6. The method of claim 5, wherein said S-nitrosothiol is administered as part of a pharmaceutical composition comprising a pharmaceutically acceptable carrier.

7. The method of claim 6, wherein said pharmaceutical composition is in the form of an injectable solution which is administered by continuous intravenous infusion.

8. A method of inhibiting platelet aggregation, comprising administering an effective amount of the S-nitrosothiol of any one of claims 1-3 to an animal in need of such treatment.

9. The method of claim 8, wherein said S-nitrosothiol is administered as part of a pharmaceutical composition comprising a pharmaceutically acceptable carrier.

10. The method of claim 9, wherein said pharmaceutical composition is in the form of an injectable solution which is administered by continuous intravenous infusion.

11. A method of inhibiting the activity of angiotensin converting enzyme comprising administering an effective amount of the S-nitrosothiol of any one of claims 1-3 to an animal in need of such treatment.

12. The method of claim 11, wherein said S-nitrosothiol is part of a pharmaceutical composition comprising a pharmaceutically acceptable carrier.

13. The method of claim 12, wherein said pharmaceutical composition is in the form of an injectable solution which is administered by continuous intravenous infusion.

14. A method of effecting vasodilation, comprising administering an effective amount of the S-nitrosothiol of any one of claims 1-3 to an animal in need of such treatment.

15. The method of claim 14, wherein said S-nitrosothiol is administered as part of a pharmaceutical composition comprising a pharmaceutically acceptable carrier.

16. The method of claim 15, wherein said pharmaceutical composition is in the form of an injectable solution which is administered by continuous intravenous infusion.

17. A method of treating toxemia of pregnancy comprising administering an effective amount of the S-nitrosothiol of any one of claims 1-3 to an animal in need of such treatment.

18. The method of claim 17, wherein said S-nitrosothiol is administered as part of a pharmaceutical composition comprising a pharmaceutically acceptable carrier.

19. The method of claim 18, wherein said pharmaceutical composition is in the form of an injectable solution which is administered by continuous intravenous infusion.

20. A method of treating sclerodema, comprising administering an effective amount of the S-nitrosothiol of any one of claims 1-3 to an animal in need of such treatment.

21. The method of claim 20, wherein said S-nitrosothiol is administered as part of a pharmaceutical composition comprising a pharmaceutically acceptable carrier.

22. The method of claim 21, wherein said pharmaceutical composition is in the form of an injectable solution which is administered by continuous intravenous infusion.

* * * * *